United States Patent [19]

Tessier et al.

[11] Patent Number: 4,737,513

[45] Date of Patent: Apr. 12, 1988

[54] NOVEL PYRROLE DERIVATIVES

[75] Inventors: Jean Tessier, Vincennes; Jean-Pierre Demoute, Montreuil Sous Bois; Laurent Taliani, Pavillons Sous Bois, all of France

[73] Assignee: Roussel Uclaf, Paris, France

[21] Appl. No.: 765,317

[22] Filed: Aug. 13, 1985

[30] Foreign Application Priority Data

Aug. 14, 1984 [FR] France ................................ 84 12791
Apr. 23, 1985 [FR] France ................................ 85 06134

[51] Int. Cl.$^4$ .................. A61K 31/40; C07D 207/325; C07D 207/333
[52] U.S. Cl. .................................... 514/427; 514/423; 514/426; 548/517; 548/526; 548/530; 548/531; 548/538; 548/539; 548/540; 548/557; 548/558; 548/561; 548/562
[58] Field of Search ............... 548/561, 562, 530, 531, 548/538, 539, 540, 557, 558; 514/427, 423, 426

[56] References Cited

U.S. PATENT DOCUMENTS

| | | | |
|---|---|---|---|
| 4,212,879 | 7/1980 | Ohsumi et al. ................... | 514/427 |
| 4,229,352 | 10/1980 | Henrick ............................. | 548/562 |
| 4,380,656 | 4/1983 | Fayter, Jr. ........................ | 548/562 X |
| 4,418,202 | 11/1983 | Fayter, Jr. et al. ............... | 548/561 X |
| 4,458,090 | 7/1984 | Fumio et al. .................... | 548/562 X |

OTHER PUBLICATIONS

C.A., 98, (1983); 98:34810c, Mitsubishi.

*Primary Examiner*—Joseph Paul Brust
*Attorney, Agent, or Firm*—Bierman and Muserlian

[57] ABSTRACT

Novel pyrrole derivatives of the formula

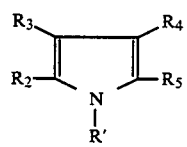

I wherein one of $R_2$ and $R_3$ is

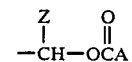

and the other of $R_2$ and $R_3$ as well as $R_4$ and $R_5$ are individually selected from the group consisting of hydrogen, halogen, alkyl of 1 to 18 carbon atoms, aryl of 6 to 14 carbon atoms, aralkyl of 7 to 18 carbon atoms, —CN, —CF$_3$, —NO$_2$, —COOAlk and Alk is alkyl of 1 to 8 carbon atoms, alkoxy of 1 to 8 carbon atoms,

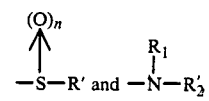

n is 0, 1 or 2, R', $R_1'$ and $R_2'$ are alkyl of 1 to 8 carbon atoms and $R_4$ and $R_5$ taken together with the carbon atoms to which they are attached may form an optionally further unsaturated carbon homocycle of up to 8 carbon atoms, Z is selected from the group consisting of hydrogen, —CN, —C≡CH, —CF$_3$ and alkyl of 1 to 3 carbon atoms, A is the residue of a pyrethrinoid acid, $R_1$ is selected from the group consisting of

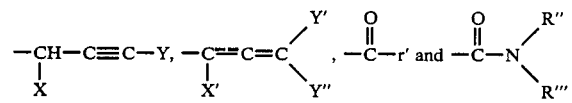

X', X, Y, Y' and Y'' are individually selected from the group consisting of hydrogen, halogen, alkyl of 1 to 8 carbon atoms and aryl of 6 to 14 carbon atoms, the dotted line indicating an optional double bond, r' is selected from the group consisting of hydrogen, alkyl of 1 to 18 carbon atoms, aryl of 6 to 14 carbon atoms, aralkyl of 7 to 18 carbon atoms, —CF$_3$, —COOAlk and alkoxy of 1 to 8 carbon atoms and Alk has the above definition, R'' and R''' are individually selected from the group consisting of hydrogen, alkyl of 1 to 8 carbon atoms, aryl of 6 to 14 carbon atoms, aralkyl of 6 to 18 carbon atoms, —CF$_3'$ —COOAlk' and alkoxy of 1 to 8 carbon atoms and Alk' is alkyl of 1 to 8 carbon atoms having pesticidal properties and novel intermediates.

51 Claims, No Drawings

NOVEL PYRROLE DERIVATIVES

OBJECTS OF THE INVENTION

It is an object of the invention to provide the novel compounds of formula I and a novel process and novel intermediates for their preparation.

It is another object of the invention to provide a novel pesticidal compositios and a novel method of combatting pests.

These and other objects and advantages of the invention will become obvious from the following detailed description.

THE INVENTION

The novel compounds of the invention are pyrrole derivatives of the formula

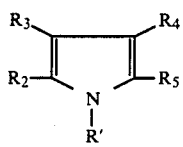

wherein one of $R_2$ and $R_3$ is

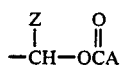

and the other of $R_2$ and $R_3$ as well as $R_4$ and $R_5$ are individually selected from the group consisting of hydrogen, halogen, alkyl of 1 to 18 carbon atoms, aryl of 6 to 14 carbon atoms, aralkyl of 7 to 18 carbon atoms, —CN, —CF$_3$, —NO$_2$, —COOAlk and Alk is alkyl of 1 to 8 carbon atoms, alkoxy of 1 to 8 carbon atoms,

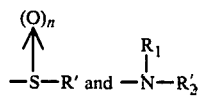

n is 0, 1 or 2, R', $R_1'$ and $R_2'$ are alkyl of 1 to 8 carbon atoms and $R_4$ and $R_5$ taken together with the carbon atoms to which they are attached may form an optionally further unsaturated carbon homocycle of up to 8 carbon atoms, Z is selected from the group consisting of hydrogen, —CN, —C≡CH, —CF$_3$ and alkyl of 1 to 3 carbon atoms, A is the residue of a pyrethrinoid acid, $R_1$ is selected from the group consisting of

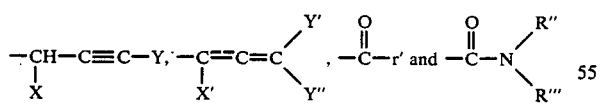

X', X, Y, Y' and Y" are individually selected from the group consisting of hydrogen, halogen, alkyl of 1 to 8 carbon atoms and aryl of 6 to 14 carbon atoms, the dotted line indicating an optional double bond, r' is selected from the group consisting of hydrogen, alkyl of 1 to 18 carbon atoms, aryl of 6 to 14 carbon atoms, aralkyl of 7 to 18 carbon atoms, CF$_3$—. —COOAlk and alkoxy of 1 to 8 carbon atoms and Alk has the above definition, R" and R"' are individually selected from the group consisting of hydrogen, alkyl of 1 to 8 carbon atoms, aryl of 6 to 14 carbon atoms, aralkyl of 6 to 18 carbon atoms, —CF$_3$—COOAlk' and alkoxy of 1 to 8 carbon atoms and Alk' is alkyl of 1 to 8 carbon atoms.

The pyrethrinoid acid from which A is derived has the formula ACOOH and is known as an intermediate for pesticidally active pyrethrinoid derivatives.

When Z is alkyl, it is preferably methyl. When one of the substituents is alkyl, it may be methyl, ethyl, n-propyl, isopropyl, n-butyl, isobutyl or n-pentyl. When one of the substituents is halogen, it is preferably fluorine, bromine or chlorine. Suitable alkoxy substituents are methoxy, ethoxy, propoxy and isopropoxy Suitable aryl substituents are phenyl optionally substituted with alkyl and alkoxy of 1 to 8 carbon atoms, —OH, —CF$_3$, —NO$_2$, —NH$_2$ or halogen. Aralkyl is preferably benzyl. In —COOAlk, Alk is preferably methyl, ethyl, propyl or isopropyl. When $R_4$ and $R_5$ together with the carbon atoms to which they are attached form a carbon homocycle, it preferably has 4 to 5 carbon atoms.

Among the preferred compounds of formula I are those wherein $R_1$ is —CH$_2$—C≡CH, those wherein Z is hydrogen or cyano, those wherein $R_2$ is

those wherein $R_2$, $R_4$ and $R_5$ are hydrogen and those wherein one of $R_2$, $R_4$ and $R_5$ is —NO$_2$, —CN or —CF$_3$.

Especially preferred compounds of formula I are those wherein A is

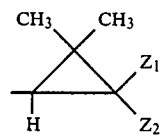

AND $Z_1$ and $Z_2$ are both methyl or $Z_1$ is hydrogen and $Z_2$ is selected from the group consisting of

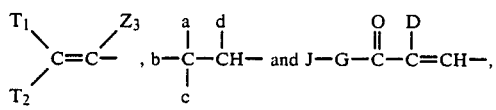

$Z_3$ is hydrogen or halogen, $T_1$ and $T_2$ are individually selected from the group consisting of hydrogen, halogen, —CF$_3$, —CN, alkyl and alkoxy of 1 to 8 carbon atoms and phenyl optionally substituted by a halogen and taken together with the carbon they are attached to form a cycloalkyl of 3 to 6 carbon atoms or

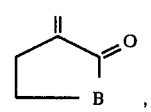

B is oxygen or sulfur, a, b, c and d are individually halogen, D is selected from the group consisting of hydrogen, halogen and alkoxy of 1 to 8 carbon atoms, G is oxygen or sulfur, J is selected from the group consisting of optionally unsaturated alkyl of 1 to 8 carbon atoms optionally substituted by one or more identical or different functional groups and optionally unsaturated cycloalkyl of 3 to 8 carbon atoms optionally substituted by one or more identical or different functional groups, optionally substituted aryl of 6 to 14 carbon atoms optionally substituted by one or more identical or different functional groups and optionally substituted heterocylic optionally substituted by one or more identical or different functional groups or A may be

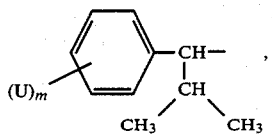

U may be halogen or alkyl or alkoxy of 1 to 8 carbon atoms and m is 0, 1 or 2.

The preferred halogens for $T_1$, $T_2$ or $Z_3$ are fluorine, chlorine or bromine and the preferred halogens for a, b, c and d are chlorine or bromine. The preferred alkyl and alkoxy for $T_1$ or $T_2$ are methyl, ethyl, n-propyl, methoxy, ethoxy or n-propoxy. The preferred halogens for D are fluorine, chlorine or bromine.

When J is alkyl substituted by a functional group, it is alkyl of 1 to 8 carbon atoms such as methyl, ethyl, propyl, isopropyl, n-butyl, isobutyl or tert.-butyl where the functional groups are defined as European Patent Application Serial No. 50,534. J may be also alkyl optionally substituted with an aryl such as optionally substituted phenyl.

Specific preferred alkyl substituted by at least one functional group, there can be cited as preferred values of J, $-(CH_2)_{n1}-CHal_3$ wherein $n_1$ is an integer from 1 to 8 and Hal is halogen, for example $-CH_2-CCl_3$, $-CH_2-CF_3$, $-CH_2-CH_2-CCl_3$ or $-CH_2-CH_2-CF_3$; $-(CH_2)_{n2}-CH\ Hal_2$ wherein Hal is defined as above and $n_2$ is an integer from 0 to 8, for example $-CH_2-CHCl_2$, $-CH_2-CHF_2$ or $-CHF_2$; $-(CH_2)_{n1}-CH_2\ Hal$ in which $n_1$ and Hal are defined as above, for example $-CH_2-CH_2Cl$ or $-CH_2-CH_2F$; $-C-(CHal_3)_3$ wherein Hal is defined as above, for example

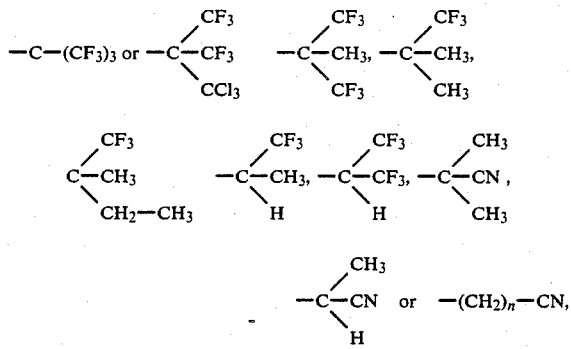

wherein n is defined as above;

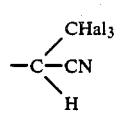

wherein Hal is defined as above, for example

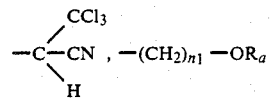

wherein $n_1$ is defined as above and $R_a$ is hydrogen or a linear or branched alkyl of 1 to 8 carbon atoms, for example $-CH_2-OCH_3$, $-CH_2-CH_2-O-CH_3$, $-CH_2-CH_2-O-CH_2-CH_3$ or $-CH_2-CH_2-OH$,

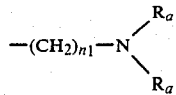

wherein $n_1$ and $R_a$ are defined as above and the two $R_a$ can be different from each other, for example

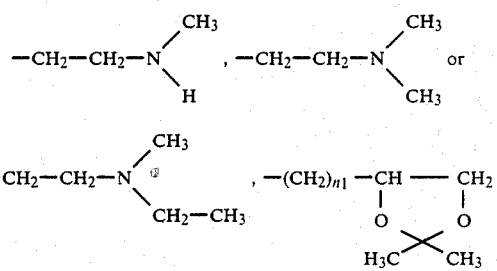

wherein $n_1$ is defined as above for example

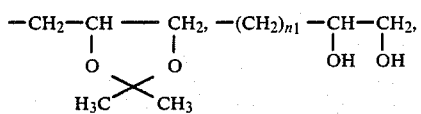

wherein $n_1$ is defined as above, for example

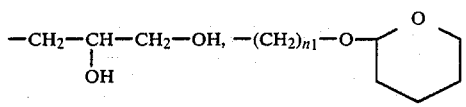

wherein $n_1$ is defined as above, for example

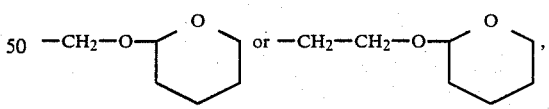

wherein $n_1$ is defined as above, for example benzyl or phenethyl,

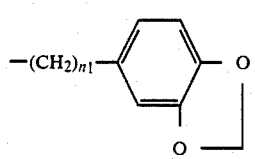

wherein $n_1$ is defined as above, for example

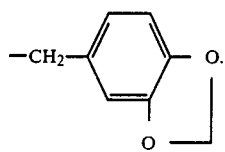

When J is an optionally substituted aryl, it is preferably an optionally substituted phenyl. When J is a heterocyclic, it is preferably a pyridyl, furanyl, thienyl, oxazolyl or thiazolyl.

Among the preferred compounds of the invention, are those wherein A is

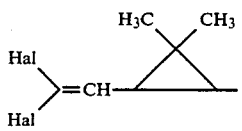

wherein Hal is halogen, for example chlorine or bromine, those wherein A is

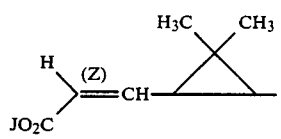

wherein J is a linear, branched or cyclized alkyl of 1 to 8 carbon atoms, the double bond having the geometry Z. In these compounds, J preferably is methyl, ethyl, n-propyl, isopropyl or tert.-butyl, those wherein A is

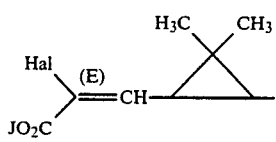

wherein Hal is halogen and J is alkyl of 1 to 8 carbon atoms with the double bond having the geometry (E). In these compounds, J preferably is methyl, ethyl, n-propyl, isopropyl or tert.-butyl.

Other preferred compounds are those wherein A is

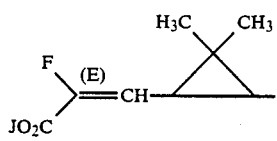

Among the specific preferred compounds of the invention are [1-(2-propynyl)-1H-pyrrol-3-yl]-methyl (1R,cis, ΔE) 2,2-dimethyl-3-(3-ethoxy-3-oxo-2-fluoro-1-propenyl)-cyclopropane carboxylate; [1-(2-propynyl)-1H-pyrrol-3-yl]-methyl (1R,cis, ΔZ) 2,2-dimethyl-3-(3-methoxy-3-oxo-1-propenyl)-cyclopropane carboxylate; [1-(2-propynyl)-2-trifluoromethyl-1H-pyrrol-3-yl]-methyl (1R,cis, ΔE) 2,2-dimethyl-3-(3-ethoxy-3-oxo-2-fluoro-1-propenyl-cyclopropane carboxylate; and [1-(2-propynyl)-2-trifluoromethyl-1H-pyrrol-3-yl]-methyl (1R,cis, ΔE) 2,2-dimethyl-3-(3-tert.-butoxy-3-oxo-2-fluoro-1-propenyl)-cyclopropane carboxylate.

The novel process of the invention for the preparation of compounds of formula I comprises reacting an alcohol of the formula

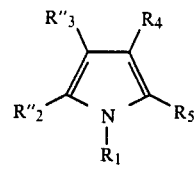

II wherein one of $R''_2$ and $R''_3$ is

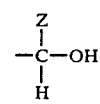

with Z retaining the same significance as above and the other of $R''_2$ or $R''_3$ as well as $R_4$ and $R_5$ having the same significance as above and $R_1$ has the same significance as above with an acid of the formula

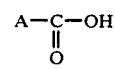

III or a functional derivative thereof with A having the above definition.

The functional derivative of the acid used is preferably an acid chloride. When the acid of formula III reacts with the alcohol, the operation is preferably effected in the presence of dicyclohexylcarbodiimide.

The compounds of formula I wherein $R_1$ includes a carbon-carbon double bond can also be prepared by a process comprising reacting the corresponding derivative including a triple bond with hydrogen in the presence of a catalyst, for example palladium on barium sulfate and quinoline.

The products of the formula

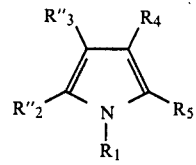

II wherein $R_1$, $R''_2$, $R''_3$, $R_4$ and $R_5$ have the above definitions are new products and are an object of the invention as new industrial products useful particularly as intermediates for the preparation of the products of formula I. The products of formula II can be obtained by introducing one or more groups on the pyrrole nucleus, or by total synthesis of this heterocycle possibly followed by the introduction of one or more functional groups on the pyrrol nucleus thus formed.

For example, the different products of formula II can be obtained as described in the examples according to the following synthesis schemes:

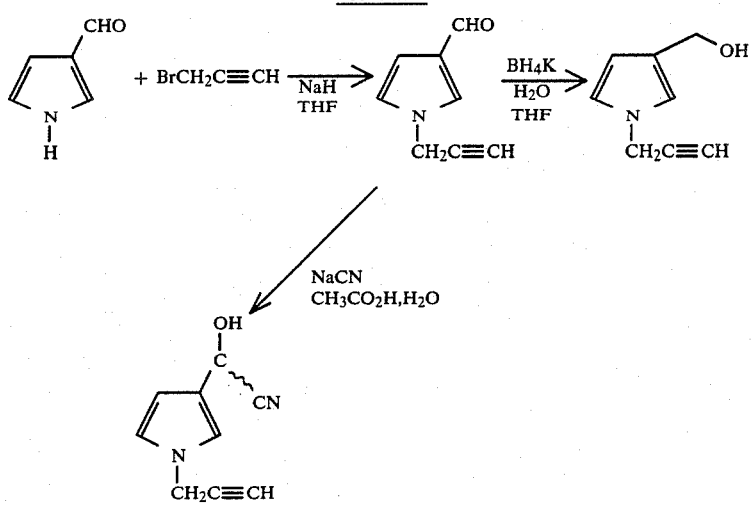
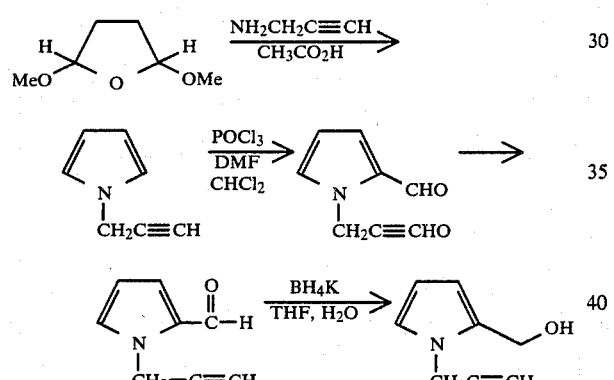
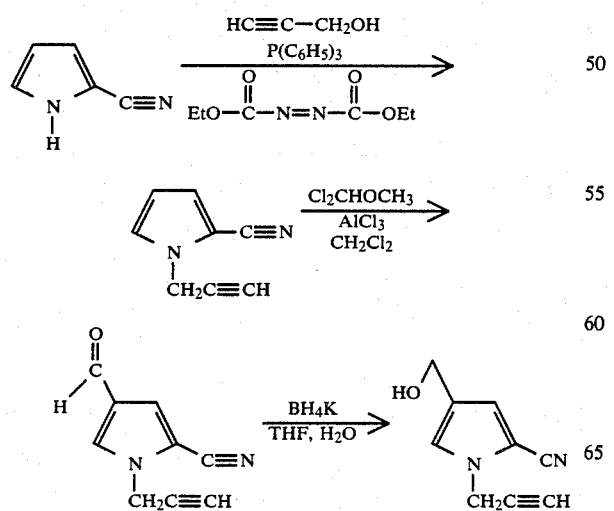
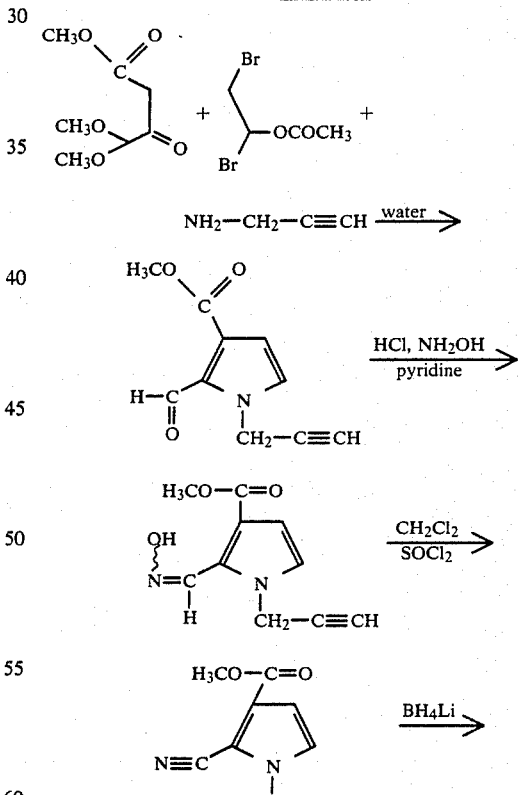
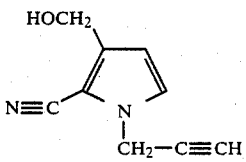

Scheme 5
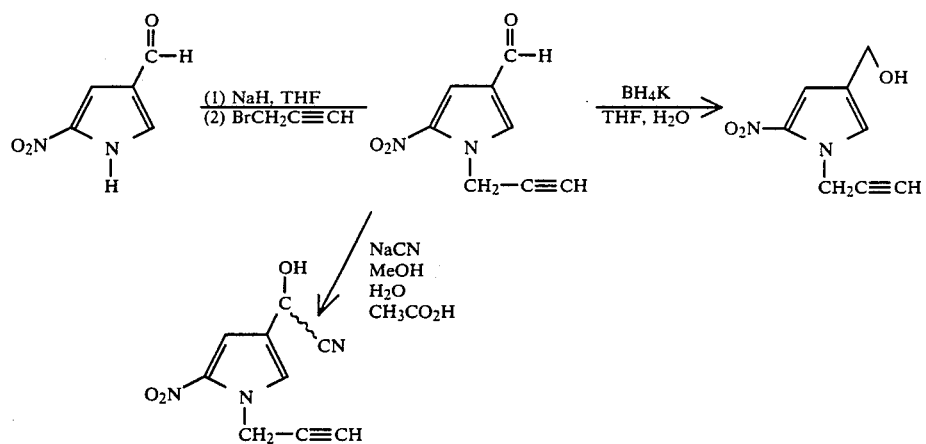
Scheme 6
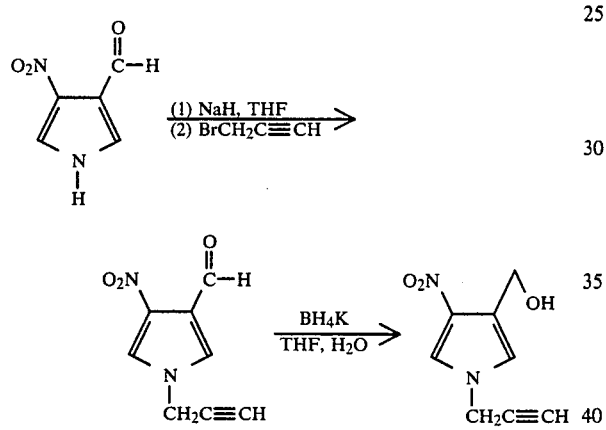
Scheme 8:
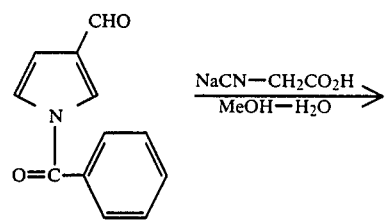
-continued
Scheme 8:
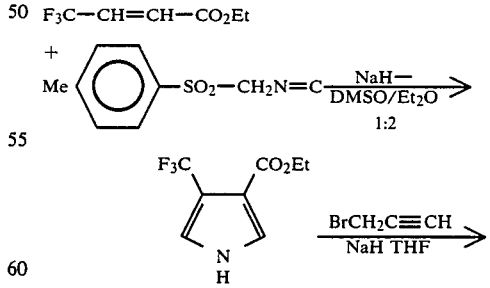
Scheme 7
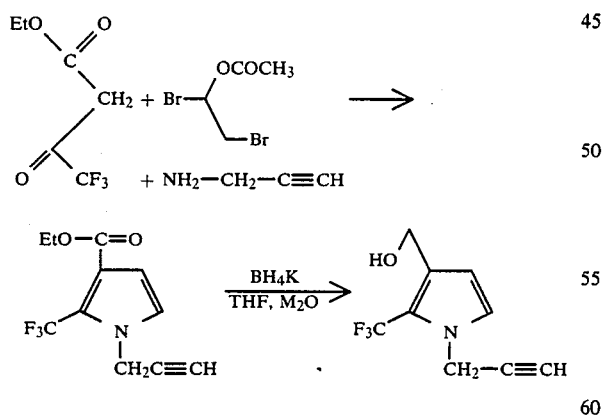
Scheme 9:
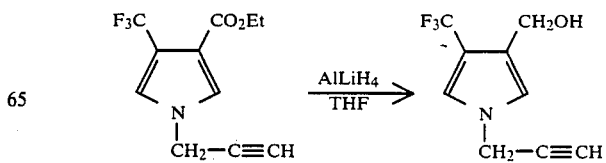
Scheme 8:
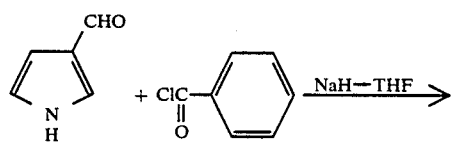

4,737,513
11
Scheme 10:
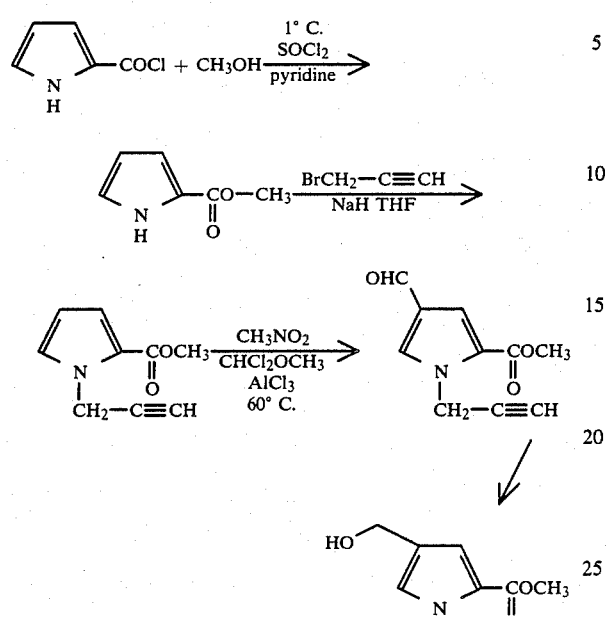
Scheme 11:
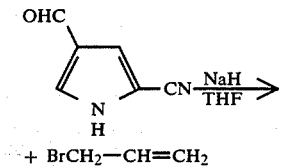
12
-continued
Scheme 11:
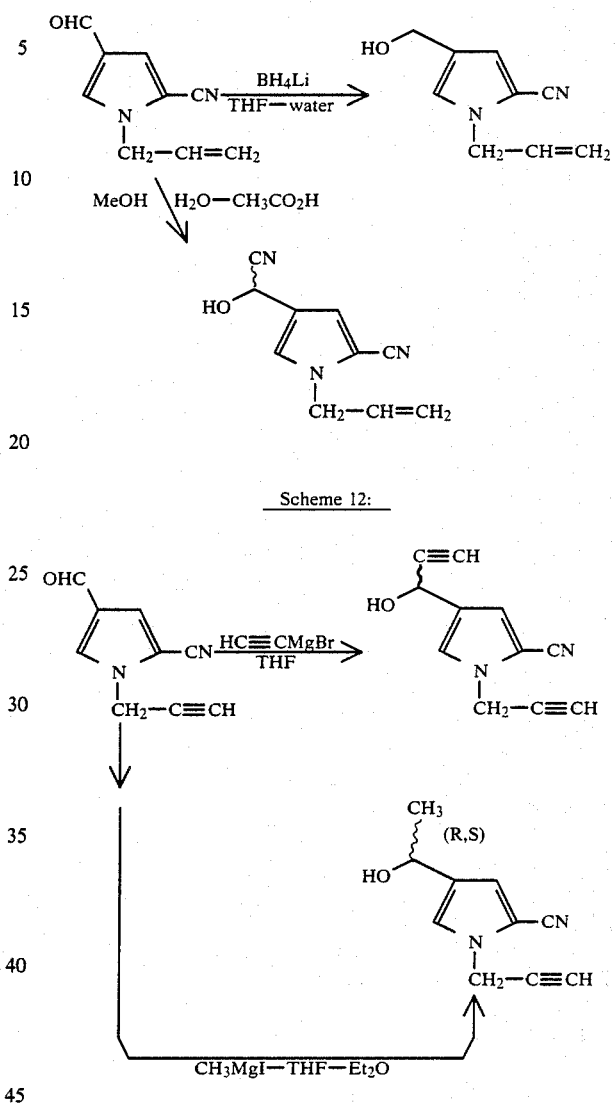
Scheme 13:
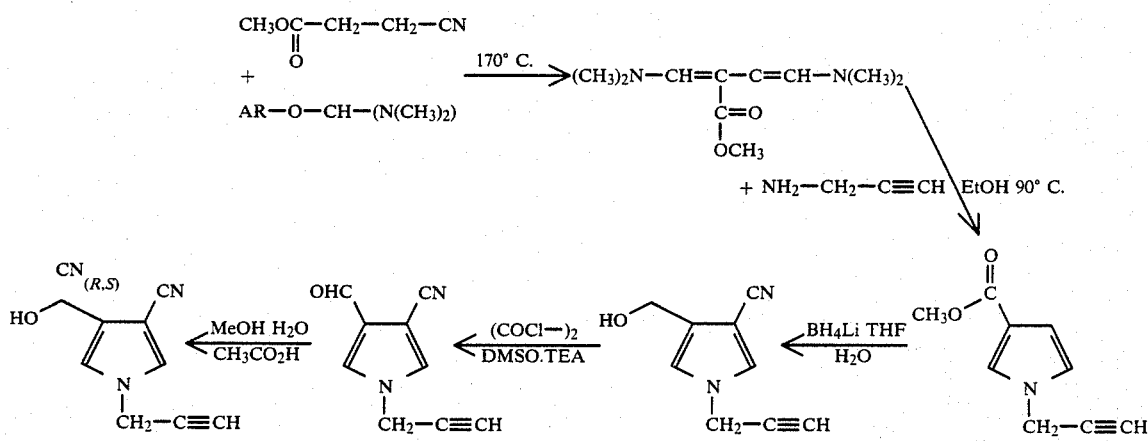

Scheme 14:

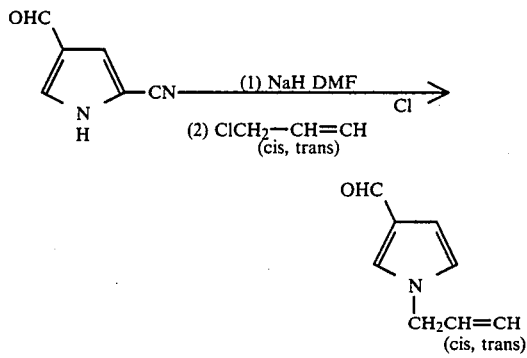

Scheme 15:

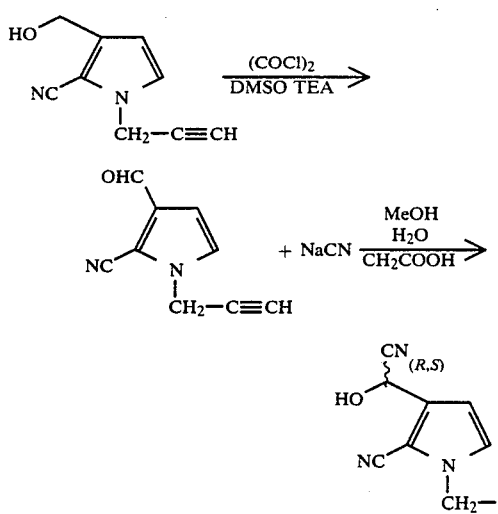

Scheme 16:

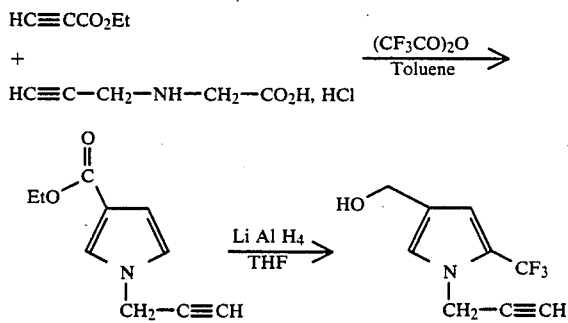

To prepare the compounds of Formula I in which Z is —CN, there can also be used a variant of the previous process called the phase transfer process described for example, in Belgian Pat. No. 851 900, which consists of reacting an aldehyde corresponding to the alcohol of Formula II and an acid of Formula III in the presence of water, of an alkaline cyanide diluted in water, of an aprotic solvent non-miscible with water and a catalyst of the phase transfer.

To prepare an alcohol of Formula II in which three of R"$_2$ or R"$_3$, R$_4$ and R$_5$ are hydrogen, there is prefera- bly used the process corresponding to scheme 1 or 2 depending on whether it is R"$_3$ or R"$_2$ which is:

To prepare an alcohol of Formula II in which the pyrrole nucleus contains a 2—CN group, the process corresponding to scheme 3 or 4 is preferred to be used depending on the respective positions of the —CN and hydroxymethyl.

To prepare an alcohol of Formula II in which the pyrrole nucleus contains a 2—NO$_2$ group, scheme 5 is preferably used. To prepare an alcohol of Formula II in which the pyrrole nucleus contains a 3—NO$_2$ group, scheme 6 is preferably used. To prepare an alcohol of Formula II in which the pyrrole nucleus contains a 2—CF$_3$ radical, a process corresponding to scheme 7 is preferably used.

The novel pesticidal compositions of the invention are comprised of a pesticidally effective amount of at least one compound of Formula I and an inert carrier. The compositions are useful to combat pests such as parasites of vegetation and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of Formula I per hectare. The compositions are also useful to combat insects in the premises for example to combat flies, mosquitoes and cockroaches.

Certain of the compounds of Formula I possess an excellent insecticidal activity and a very good knock-down power and the products of Examples 1, 2, 15 and 40 are particularly remarkable on this point.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as saroptic scabies, psoroptic scabies and choriotic scabies. The compounds of Examples 38 to 40 have remarkable acaricidal properties.

The invention also includes compositions intended to combat parasites of warm-blooded animals, parasites of premises and parasites of vegetables containing at least one compound of Formula I, and especially of Formula I$_A$.

The invention particularly includes insecticidal compositions containing as active principle at least one compound of Formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of Formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of Formula I is placed in a heating apparatus such as an electromosquito destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of the invention in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxybenzene (piperonyl butoxide) or N-(2-ethyl-heptyl-bicyclo-[2,2-1] 5-heptene-2,3-dicarboximide or piperonyl-bis-2-(2'-n-butoxy-ethoxy)-ethyl acetal (tropital).

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal associations containing as an active ingredient at least one compound of Formula I and as a second active ingredient at least one pyrethrinoid ester selected from the group consisting of esters of allethrolones, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of Formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of Formula I.

In the following examples there are described several preferred embodiments to illustrate the invention. However, it should be understood that the invention is not intended to be limited to the specific embodiments.

EXAMPLE 1

[1-(2-propynyl)-1H-pyrrol-3-yl]-methyl (1R,cisΔZ) 2,2-dimethyl-3-(3-methoxy-3-oxo-1-propenyl)-cyclopropane carboxylate STEP A: 1-(2-propynyl)-1H-pyrrole-3-carboxaldehyde 2.924 g of pyrrole-3-carboxaldehyde (J. Org. Chem. 1981, Vol. 46, p. 839) dissolved in 45 ml of tetrahydrofuran and 1.488 g of sodium hydride as 50% in oil were admixed and then were stirred for 10 minutes cold, then for 40 minutes at room temperature. After cooling, 2.5 ml of propargyl bromide were added with stirring at 5 C. for 90 minutes. A further 2 ml of propargyl bromide were added with stirring at 5° C. for 1 hour and the mixture was poured into water and extracted with methylene chloride. The solvent was distilled off at atmospheric pressure to obtain 2.868 g of 1-(2-propynyl)-1H-pyrrole-3-carboxaldehyde which was purified by chromatography on silica gel and elution with a 65-35 hexane-ethyl acetate mixture to obtain 2.868 g of the said product.

STEP B: 1-(2-propynyl)-1H-pyrrole-3-methanol 3.1 g of the product of Step A were dissolved in a solution of 90 ml of tetrahydrofuran and 19 ml of water and the solution was stirred at ambient temperature for 15 minutes. 2.517 g of boron and potassium hydride were added and after stirring at ambient temperature for 5½ hours, the reaction mixture was poured into a saturated aqueous solution of sodium chloride and then extracted with methyl chloride. The organic phase was dried and concentrated to dryness at 20° C. to obtain 3.4 g of crude 1-(2-propynyl)-1H-pyrrole-3-methanol which was used as is.

STEP C: [1-(2-propynyl)-1H-pyrrol-3-yl]-methyl (1R,cis,ΔZ) 2,2-dimethyl-3-(3-methoxy-3-oxo-1-propenyl)-cyclopropane carboxylate 542 mg of 3-(1-(2-propynyl)-pyrrolyl)-methanol were dissolved in 10 ml of methylene chloride and then while cooling to 0° to 5° C., 795 mg of (1R,cis) 2,2-dimethyl-3-(3-oxo-3-methoxy-1 (ΔZ) propenyl)-cyclopropane carboxylic acid were added thereto with stirring over 10 minutes. A solution containing 8 ml of methylene chloride, 835 mg of dicyclohexylcarbodiimide and 5 mg of 4-dimethylamino-pyridine was added dropwise at 7° C. and when the addition was finished, the reaction mixture was allowed to return to ambient temperature and was stirred for 16 hours and filtered. The filtrate was concentrated to dryness and the residue was taken up in ether and filtered to eliminate the insoluble matter. The filtrate was concentrated to dryness to obtain 1.112 g of a crude product. The residue was chromatographed over silica gel and was eluted with a hexane-isopropyl ether mixture (55-45) with 2% of triethylamine to obtain a product which was crystallized from isopropyl ether to obtain 700 mg of [1-(2-propynyl)-1H-pyrrol-3-yl]-methyl (1R,cis,ΔZ) 2,2-dimethyl-3-(3-methoxy-3-oxo-1-propenyl)-cyclopropane carboxylate with a specific rotation of $[\alpha]_D = +23° \pm 2°$ (c=0.3% in toluene).

EXAMPLE 2

[1-(2-propynyl)-1H-pyrrol-3-yl]-methyl (1R,cisΔE) 2,2-dimethyl-3-(3-ethoxy-3-oxo-2-fluoro-1-propenyl)-cyclopropane carboxylate Using the procedure of Example 1, the following reaction was effected to obtain the title compound

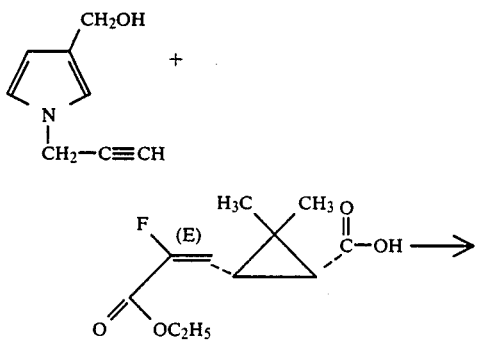
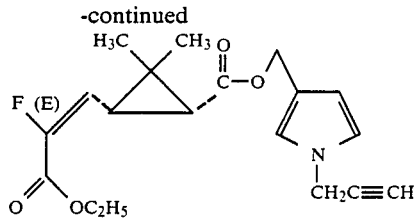

$\alpha_D = +5° \pm 2°$ (c=0.3% toluene)

EXAMPLE 3

[1-(2-propynyl)-1H-pyrrol-3-yl]-methyl (1R,cis,ΔZ) 2,2-dimethyl-3-(3-tert-butyloxy-3-oxo-1-propenyl)-cyclopropane carboxylate Using the procedure of Example 1, the following reaction was effected to obtain the title compound.

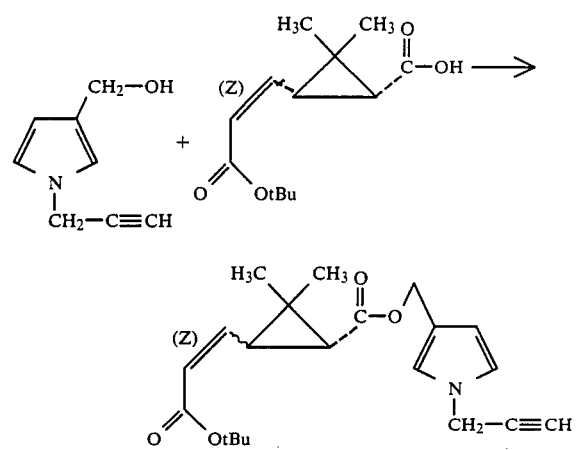

m.p. = 104° C. $\alpha_D = +33° \pm 1.5°$ (c=1% in toluene)

EXAMPLE 4

[1-(2-propynyl)-1H-pyrrol-3-yl]-methyl (1R,cisΔE) 2,2-dimethyl-3-(3-methoxy-3-oxo-2-fluoro-1-propenyl)-cyclopropane carboxylate Using the procedure of Example 1, the following reaction was effected to obtain the title compound.

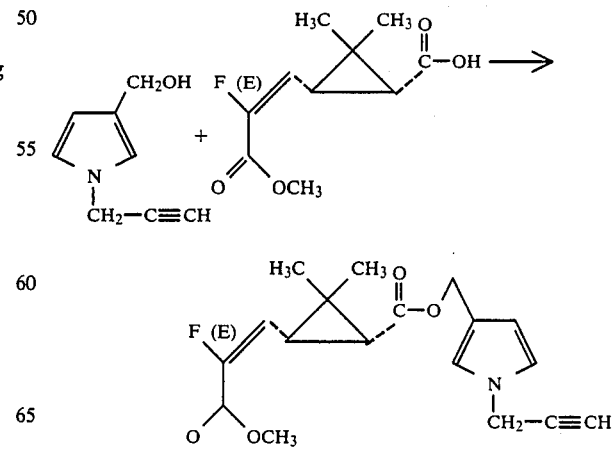

$\alpha_D = +15° \pm 3°$ (c=0.3% in toluene)

EXAMPLE 5

[1-(2-propynyl)-1H-pyrrol-3-yl]-methyl (1R,cis,ΔE) 2,2-dimethyl-3-(3-tert-butoxy-3-oxo-2-fluoro-1-propenyl)-cyclopropane carboxylate Using the procedure of Example 1, the following reaction was effected to obtain the title compound.

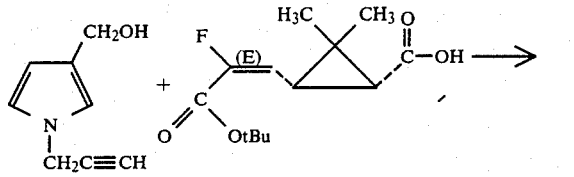

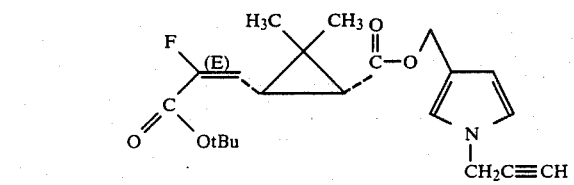

m.p.=63° C. $\alpha_D = +19,5° \pm 1.5°$ (c=1% in toluene)

EXAMPLE 6

[1-(2-propynyl)-1H-pyrrol-3-yl]-methyl (1R,cis) 2,2-dimethyl-3-(-dibromoethenyl)-cyclopropane carboxylate

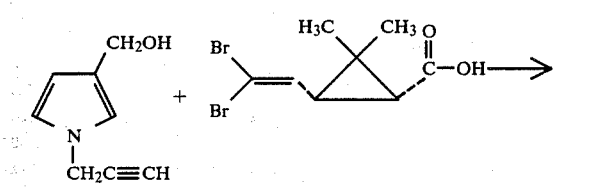

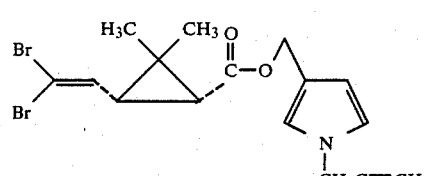

$\alpha_D = -15.5°$ (c=0.5% toluene)

EXAMPLE 7

[1-(2-propynyl)-1H-pyrrol-3-yl]-methyl (1R,cis,ΔZ) 2,2-dimethyl-3-(3-ethoxy-3-oxo-1-propenyl)-cyclopropane carboxylate Using the procedure of Example 1, the following reaction was effected to obtain the above compound.

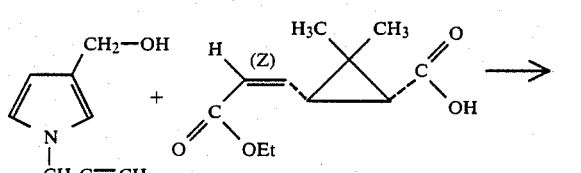

-continued

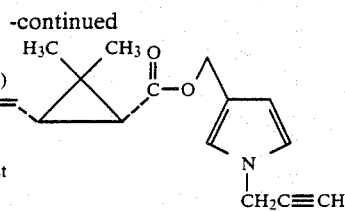

m.p.=50° C. $\alpha_D = +23° \pm 1°$ (c=1% toluene)

EXAMPLE 8

1-[1-(2-propynyl)-1H-pyrrol-3-yl]-methyl (1R,trans) 2,2-dimethyl-3-(2,2-difluoroethenyl)-cyclopropane carboxylate Using the procedure of Example 1, the following reaction was effected to produce the above compound.

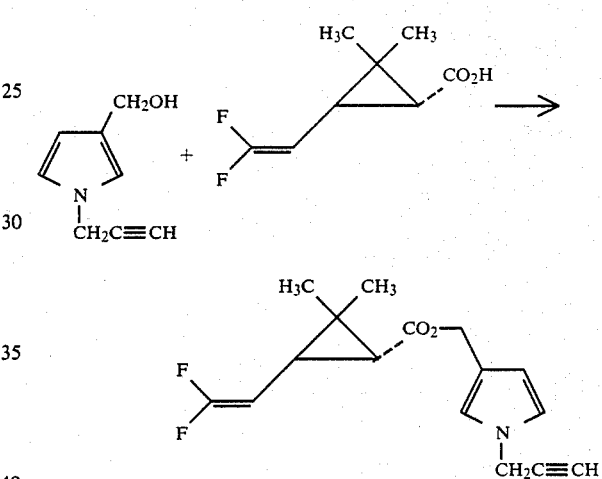

$\alpha_D = -34° \pm 1°$ (c=1.5% in toluene)

EXAMPLE 9

1-[1-(2-propynyl)-1H-pyrrol-3-yl]-methyl (1R,cis) 2,2-dimethyl-3-(2,2-difluoroethenyl)-cyclopropane carboxylate Using the procedure of Example 1, the following reaction was effected to obtain the above compound.

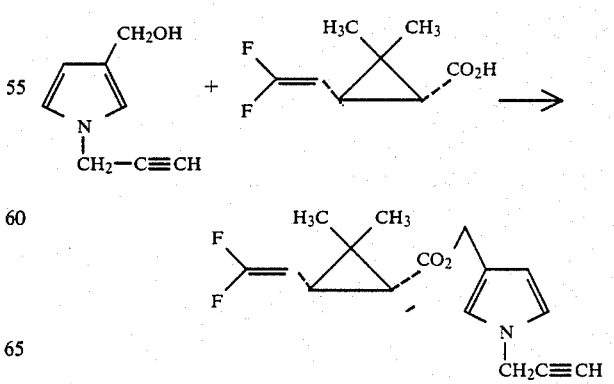

$\alpha_D = -27° \pm 2°$ (c=0.5% in toluene)

EXAMPLE 10

[1-(2-propynyl)-1H-pyrrol-3-yl]-methyl 2,2-dimethyl-3,3-dimethyl-cyclopropane carboxylate Using the procedure of Example 1, the following reaction was effected to obtain the above compound.

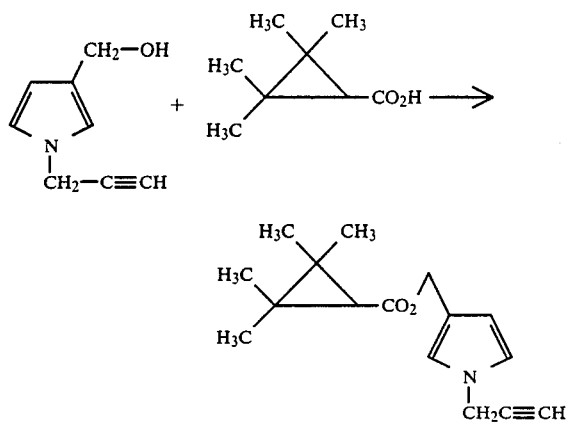

EXAMPLE 11

[1-(2-propynyl)-1H-pyrrol-3-yl]-methyl [2S] 2-(4-difluoromethoxyphenyl)-3-methyl butyrate Using the procedure of Example 1, the following reaction was effected to obtain the above compound.

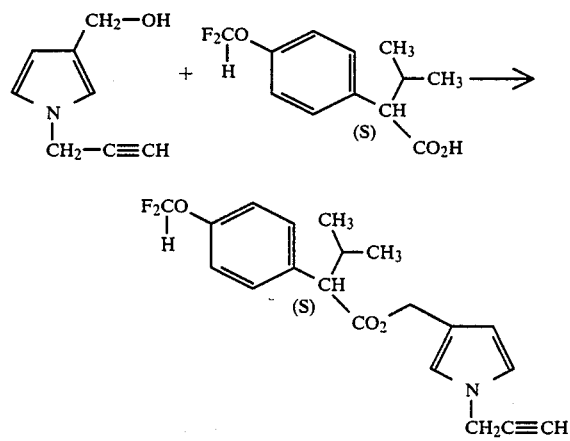

$\alpha_D = +5° \pm 4°$ (c=0.3% in toluene)

EXAMPLE 12

[1-(2-propynyl)-1H-pyrrol-3-yl]-methyl (1R,trans$\Delta Z$ and $\Delta E$) 2,2-dimethyl-3-(3,3,3-trifluoro-2-chloro-1-propenyl)-cyclopropane carboxylate Using the procedure of Example 1, the following reaction was effected to obtain the above compound.

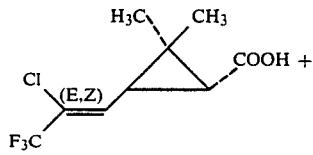

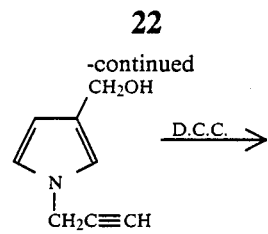

$\alpha_D = +6.5° \pm 4°$ (c=0.3% in toluene)

EXAMPLE 13

(R,S)-cyano-[1-(2-propynyl)-1H-pyrrol-3-yl]-methyl (1R,cis) 2,2-dimethyl-3-(2,2-dibromoethenyl)-cyclopropane carboxylate which was separated into its two isomers, A and B

STEP A:

α-hydroxy-1-(2-propynyl)-1H-pyrrole-3-acetonitrile 0.44 ml of acetic acid was added to a solution of 510 mg of the product of Step B of Example 1, 7 ml of methanol and 2 ml of water another 0.44 ml of acetic acid was added. The mixture was cooled to 20° C. and 2.82 mg of sodium cyanide were added, after which the mixture was stirred for 90 minutes at 20° C., then cooled to ±10° C. Another 1.4 g of sodium cyanide and 2.2 ml of acetic acid were added and after stirring for 4 hours, the reaction mixture was poured into water and extracted with ethyl acetate. The organic phase was washed with water and dried, then concentrated to dryness to obtain 590 mg of α-hydroxy-1-(2-propynyl)-1H-pyrrole-3-acetonitrile.

Using the procedure of Example 1, the following reaction was effected to obtain the desired compound.

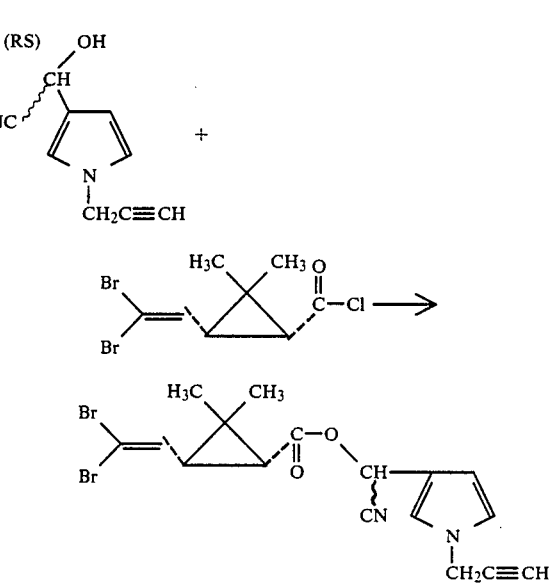

$\alpha_D = -2° \pm 2°$ (c=0.2% in toluene)

EXAMPLE 14

(R,S)-cyano-[1-(2-propynyl)-1H-pyrrol-3-yl]-methyl (1R,cis,ΔZ) 2,2-dimethyl-3-(3-methoxy-3-oxo-1-propenyl)-cyclopropane carboxylate Using the procedure of Example 1, the following reaction was effected to obtain the above compound.

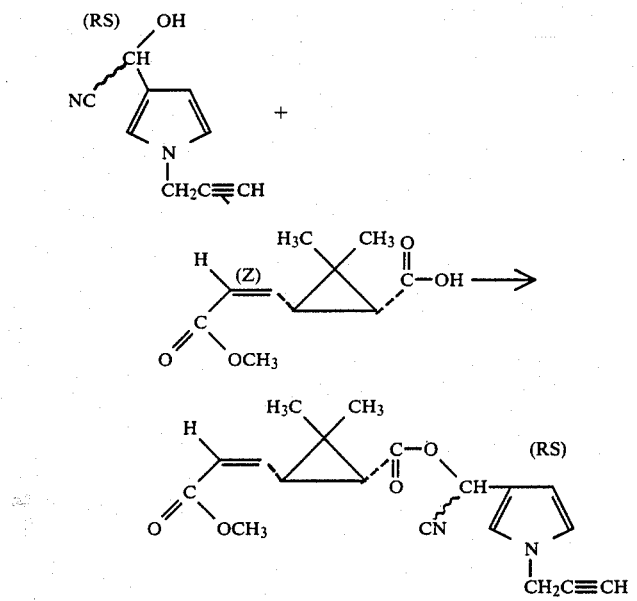

$\alpha_D = +24° \pm 2°$ C. (c=0.5% in toluene)

EXAMPLE 15 cyano-[1-(2-propynyl)-1H-pyrrol-3-yl]-methyl (1R,cisΔE) 2,2-dimethyl-3-(3-ethoxy-3-oxo-2-fluoro-1-propenyl)-cyclopropane carboxylate (A and B isomers)

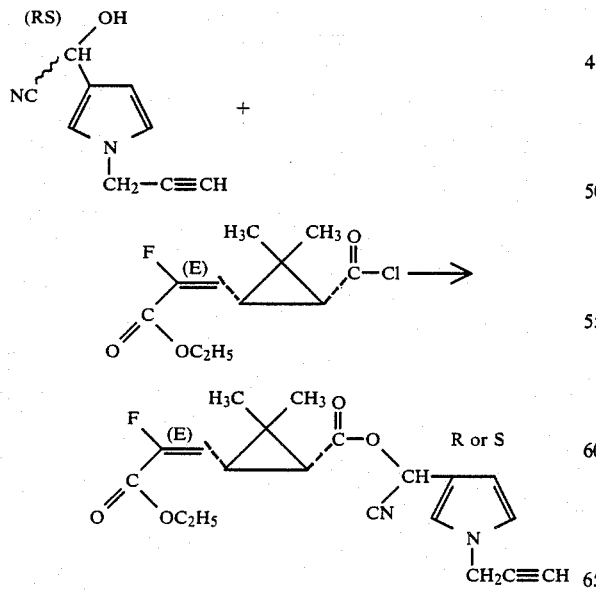

$\alpha_D = -4.5° \pm 2°$ (c=0.3% in toluene) or $+42° \pm$ (c=0.5% in toluene)

EXAMPLE 16

(R,S)-cyano-[1-(2-propynyl)-1H-pyrrol-3-yl]-methyl isopropyl-4-chlorophenyl acetate

STEP A: 1,2-propynyl pyrrole 10.32 g of propargylamine and 24.76 g of 2,5-dimethoxyhydrofuran were added to 38 ml of acetic acid in a heating bath which was at 110° C. with stirring which was continued for three quarters of an hour. The mixture was poured into 250 ml of water, and 345 ml of 2N sodium hydroxide were added. After extraction with ether, the organic phase was dried and concentrated to dryness to obtain 15 g of residue which was chromatographed over silica. Elution with a hexane-ethyl acetate (8-2) mixture and concentration at 30° C. under reduced pressure yielded 10 g of 1,2-propynyl pyrrole.

STEP B: 2-(1-(2-propynylpyrrolyl-carboxaldehyde 16 g of phosphorus oxychloride were added to 7.64 g of dimethylformamide and then 50 ml of methylene chloride were added with stirring at 0° C. for half an hour. Then at 0° C., a solution of 11 g of 1-(2-propynyl)-pyrrole carboxaldehyde in 40 ml of methylene chloride was added and the mixture was refluxed for half an hour. It was then cooled to 20° C. and an aqueous solution of sodium acetate (58.6 g in 117 ml) was added. The mixture was refluxed for a quarter of an hour with good stirring and was extracted with methylene chloride. The organic phase was washed with water, dried and concentrated to dryness. The residue was chromatographed over silica and eluted with a hexane-ethyl acetate (6-4) mixture to obtain 9.3 g of 2-(1-2-propynylpyrrolyl)-carboxaldehyde.

STEP C: 2-[1-(2-propynyl)-pyrrolyl]-methanol 0.7 g of potassium borohydride was added to a solution of 1.75 g of the product of Step B, 50 ml of tetrahydrofuran and 10 ml of water. After stirring for 1 hour at 20° C., 0.35 g of potassium borohydride was added, and the stirring was continued for half an hour at 20° C. The solution was then saturated with sodium chloride and extracted with ethyl acetate. The combined organic phases were dried and evaporated to dryness at 40° C. under reduced pressure to obtain 1.78 g of 2-[1-(2-propynyl)-pyrrolyl]-methanol.

STEP D: (R,S) cyano-[1-(2-propynyl)-1H-pyrrol-3-yl]-methyl isopropyl-4-chlorophenyl acetate Using the procedure of Example 1, the following reaction was effected to obtain the above compound.

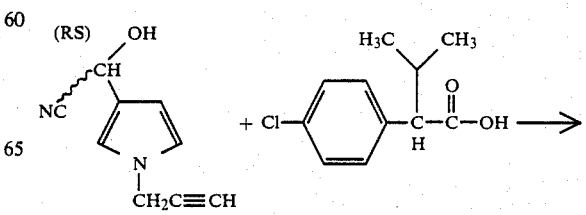

-continued

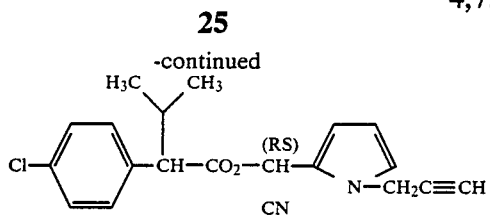

$\alpha_D = -20.5° \pm 2°$ (C=0.5% in toluene)

EXAMPLE 17

[1-(2-propynyl)-1H-pyrrol-2-yl]-methyl (1R,cis) 2,2-dimethyl-3-(2,2-dibromoethenyl)-cyclopropane carboxylate

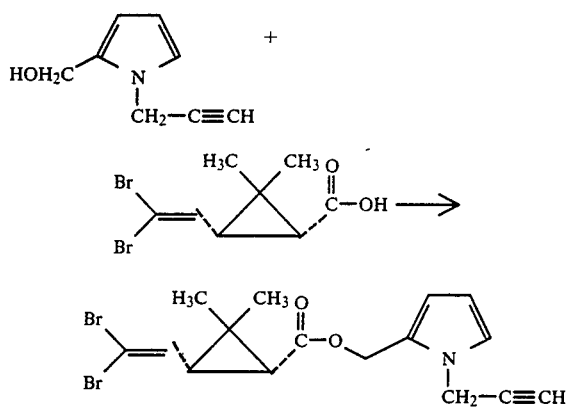

$[\alpha]_D = -12° \pm 1°$ (c=1% in toluene).

EXAMPLE 18

2-cyano-[1-(2-propynyl)-1H-pyrrol-4-yl]-methyl (1R,cisΔE)
2,2-dimethyl-3-(3-ethoxy-3-oxo-2-fluoro-1-propenyl)-cyclopropane carboxylate STEP A: 1-(2-propynyl)-1H-pyrrole-2-carbonitrile 51.57 g of 2-cyano-pyrrol[prepared by the process of Can. J. Chem. Vol. 59, p. 2763 (1981)], 146.9 g of triphenylphosphine, and 43.95 g of propargyl alcohol were mixed together and 420 ml of tetrahydrofuran were added. The mixture was cooled at +5° C., and over half an hour at 0° to 5° C., 97.5 g of ethyl azodicarboxylate were introduced. The temperature was allowed to return to ambient, and stirring was maintained for 18 hours. The solvent was evaporated under reduced pressure, and the crystallized residue was taken up in ethyl ether and filtered. After concentrating the filtrate, an oil was obtained which was chromatographed over silica. Elution with a hexane-ethyl acetate (7–3) mixture yielded 34 g of 1-(2-propynyl)-1H-pyrrole-2-carbonitrile.

STEP B:
4-formyl-[(2-propynyl)]-1H-pyrrole-2-carbonitrile

A mixture of 2.36 g of aluminium chloride in 6 ml of anhydrous methylene chloride was cooled to −78° C. and 1.3 g of the product of Step A in solution in 8 ml of methylene chloride and 0.5 ml of nitromethane were added. 1.49 g of dichloromethyl ether in solution in 15 ml of methylene chloride were added at −55° C. and the reaction mixture was kept for 1 hour at −60° C., then allowed to return to 20° C., at which temperature it was held for 18 hours. It was poured into water, stirred, and neutralized to pH 7 by addition of 33 ml of 2N sodium hydroxide. Extraction was with methylene chloride and the extracts were washed with a 1M potassium bicarbonate solution, dried and concentrated to dryness to obtain 1.5 g of 4-formyl-[(2-propynyl)]-1H-pyrrole-2-carbonitrile which was washed with dupentane and dried to obtain 1.1 g of the said product melting at 97° C.

STEP C:
4-(hydroxymethyl)-1-(2-propynyl)-1H-pyrrol-2-carbonitrile 372 mg of potassium borohydride were added to a solution of 546 mg of the product of Step B in 40 ml of tetrahydrofuran and 5.5 ml of water. After stirring at ambient temperature for a quarter of an hour, 50 ml of a saturated aqueous solution of sodium chloride were added. By extraction with ethyl acetate, drying and concentrating the extracts to dryness, 600 mg of 4-(hydroxymethyl)-1-(2-propynyl)-1H-pyrrol-2-carbonitrile were obtained.

STEP D:
2-cyano[1-(2-propynyl)-1H-pyrrol-4-yl]-methyl (1R,cisΔE)
2,2-dimethyl-3-(3-ethoxy-3-oxo-2-fluoro-1-propenyl)-cyclopropane carboxylate Using the procedure of Example 1, the following reaction was effected to obtain the above compound.

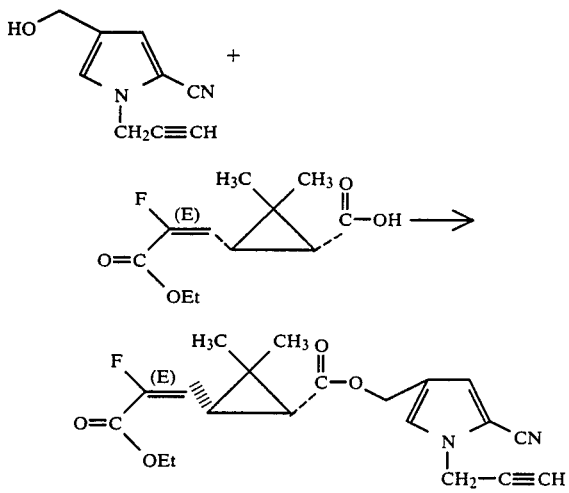

$\alpha_D = 30° \pm 2°$ (c=0.5% in toluene)

EXAMPLE 19

2-cyano[1-(2-propynyl)-1H-pyrrol-4-yl]-methyl (1R,cis) 2,2-dimethyl-3-(2,2-dibromoethenyl)-cyclopropane carboxylate Using the procedure of Example 1, the following reaction was effected to obtain the above compound,

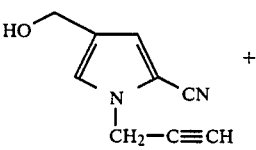

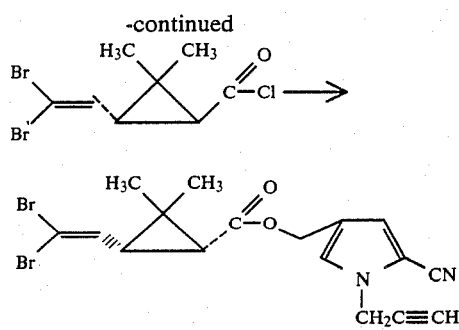

$\alpha_D = -3° \pm 2°$ (c=0.5% in toluene)

EXAMPLE 20

2-cyano-[1-(2-propynyl)-1H-pyrrol-4-yl]-methyl (1R,cis) 2,2-dimethyl-3-(3-methoxy-3-oxo-1-propenyl)-cyclopropane carboxylate Using the procedure of Example 1, the following reaction was effected to obtain the above compound.

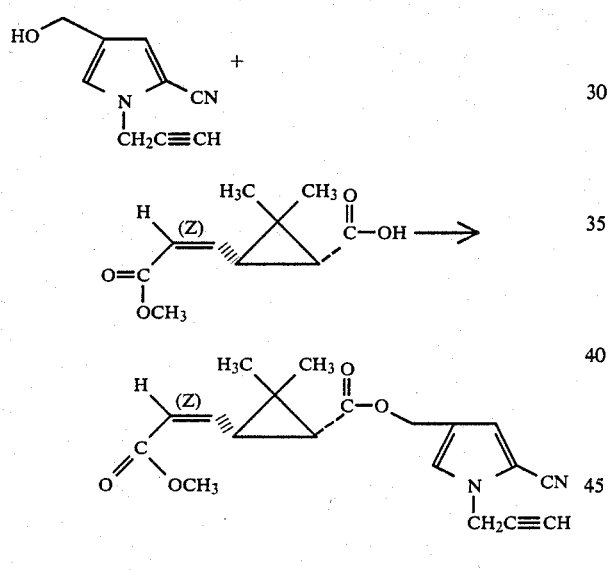

$\alpha_D = +55.5° \pm 2°$ (c=0.5% in toluene)

EXAMPLE 21

2-cyano-[1-(2-propynyl)-1H-pyrrol-4-yl]-methyl (1R,cisΔE) 2,2-dimethyl-3-(3-terbutoxy-3-oxo-2-fluoro-1-propenyl)-cyclopropane carboxylate Using the procedure of Example 1, the following reaction was effected to obtain the above compound.

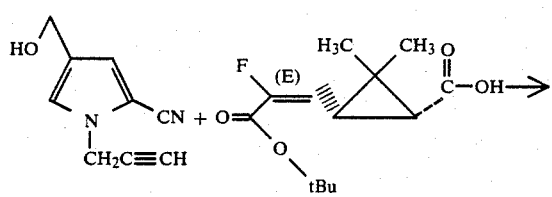

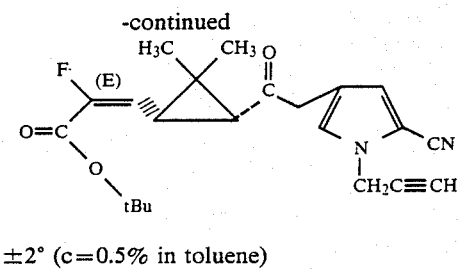

$\alpha_D = +35° \pm 2°$ (c=0.5% in toluene)

EXAMPLE 22

(R,S)-cyano-[2-cyano-1-(2-propynyl)-1H-pyrrol-4-yl]-methyl (1R, cis) 2,2-dimethyl-3-(2,2-dibromoethenyl)-cyclopropane carboxylate 447 mg of 4-formyl-1-(2-propynyl)-1H-pyrrol-2-carbonitrile were poured into 13 ml of toluene and then there was added 173 mg of sodium cyanide, 38 mg of tetrabutylammonium bromide, 894 mg of (1R,cis) 2,2-dimethyl-3-(2,2-dibromoethenyl)-cyclopropane carboxylic acid chloride and 0.13 ml of water. After stirring at 20° C. for 18 hours, 100 ml of benzene were added, and the mixture was dried and concentrated to dryness to obtain 1017 mg of (R,S)-cyano-[2-cyano-1-(2-propynyl)-1H-pyrrol-4-yl]-methyl (1R,cis) 2,2-dimethyl-3-(2,2-dibromoethenyl)-cyclopropane carboxylate with a specific rotation of $[\alpha]_D = +9° \pm 2°$ (c=0.3% toluene).

EXAMPLE 23 cyano-[2-cyano-1-(2-propynyl)-1H-pyrrol-4-yl]-methyl (1R,cisΔZ) 2,2-dimethyl-3-(3-methoxy-3-oxo-1-propenyl)-cyclopropane carboxylate Using the procedure of Example 1, the following reaction was effected to obtain the above compound,

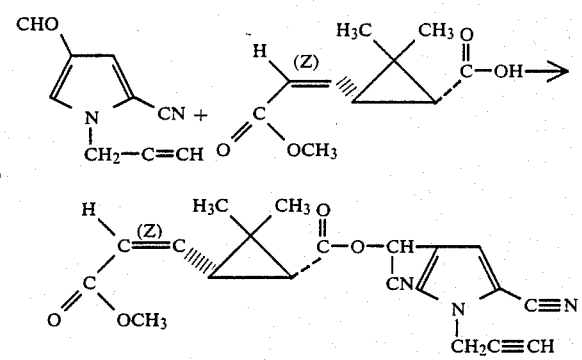

$\alpha_D = +53.5° \pm 2°$ (c=0.5% toluene)

EXAMPLE 24 cyano-[2-cyano-1-(2-propynyl)-1H-pyrrol-4-yl]-methyl (1R,cisΔE) 2,2-dimethyl-3-(3-ethoxy-3-oxo-2-fluoro-1-propenyl)-cyclopropane carboxylate Using the procedure of Example 1, the following reaction was effected to prepare the above compound,

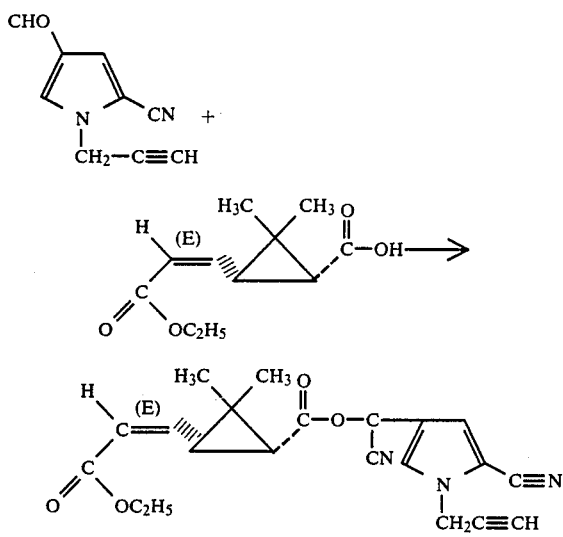

αD = +40°±1° (c=1% in toluene)

EXAMPLE 25 cyano-[2-cyano-1-(2-propynyl)-1H-pyrrol-4-yl]-methyl (1R,cisΔE) 2,2-dimethyl-3-(3-terbutoxy-3-oxo-2-fluoro-1-propenyl)-cyclopropane carboxylate

STEP A: methyl 2-formyl-1-(2-propynyl)-1H-pyrrole-3-carboxylate

A solution of 7.05 g of methyl 1,1-dimethoxy-2-oxobutanoate and 4,4 g of propargylamine in 20 ml of water was cooled to 20° C. and stirred for 10 minutes. Then 9.9 g of 1,2-dibromoethyl acetate were added dropwise and the mixture was stirred at 20° C. for 24 hours. The mixture was poured into water and extracted with ethyl acetate. The organic extracts were washed with a sodium bicarbonate solution, dried and concentrated to dryness to obtain 10 g of residue which was chromatographed over silica. Elution with a cyclohexane-ethyl acetate mixture (75–25) yielded 1.9 g of methyl 2-formyl-1-(2-propynyl)-1H-pyrrole-3-carboxylate which melted at 76° C.

STEP B: methyl 1-(2-propynyl)-2-oximinomethyl-3-pyrrole-carboxylate 2 g of the product of Step A, 725 mg of hydroxylamine hydrochloride and 11 ml of anhydrous pyridine were stirred for 3 hours at ambient temperature and the pyridine was then concentrated under reduced pressure. The residue was taken up in ethyl acetate and the solution was washed with water, dried and concentrated to obtain 2.3 g of methyl 1-(2-propynyl)-2-oximinomethyl-3-pyrrole-carboxylate melting at 88°–90° C.

STEP C: methyl 2-cyano-1-(2-propynyl)-1H-pyrrole-3-carboxylate

A solution obtained by mixing 3.54 g of thionyl chloride in solution in 2 ml of methylene chloride and 2.2 g of the product of Step B in 15 ml of methylene chloride was cooled to 20° C. The reaction mixture was stirred at ambient temperature for 24 hours, then concentrated to obtain 1.8 g of residue which was chromatographed over silica. Elution with a cyclohexaneethyl acetate mixture (7–3) yielded. 1.430 g of methyl 2-cyano-1-(2-propynyl)-1H-pyrrole-3-carboxylate melting at 112° C.

STEP D: 3-(hydroxymethyl)-1-(2-propynyl)-1H-pyrrole-2-carbonitrile

A mixture of 830 mg of the product of Step C, 8 ml of tetrahydrofuran and 2 ml of water was stirred for 24 hours at 20° C. and then 280 mg of lithium borohydride were added. After adding 30 ml of ethyl acetate, drying and concentrating to dryness, 750 mg of residue was obtained which was chromatographed over silica. Elution with a mixture of cyclohexane and ethyl acetate (6–4) yielded 138 mg of 3-(hydroxymethyl)-1-(2-propynyl)-1H-pyrrole-2-carbonitrile melting at 65° C.

STEP E: cyano-[2-cyano-1-(2-propynyl)-1H-pyrrol-4-yl]-methyl (1R,cis,ΔE) 2,2-dimethyl-3-(3-tert.-butoxy-3-oxo-2-fluoro-1-propenyl)-cyclopropane carboxylate Using the procedure of Example 1, the following reaction was effected to obtain the above compound.

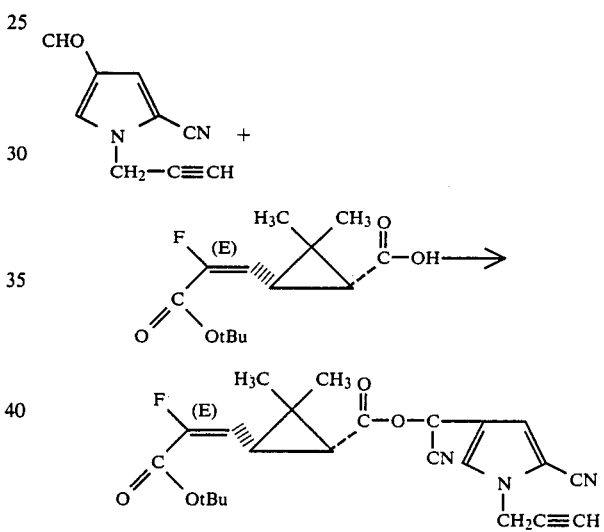

αD = +39°±1° (c=1% in toluene)

EXAMPLE 26

[1-(2-propynyl)-2-cyano-1H-pyrrol-3-yl]-methyl (1R,cis) 2,2-dimethyl-3-(2,2-dibromoethyl)-cyclopropane carboxylate Using the procedure of Example 1, the following reaction was effected to obtain the above compound.

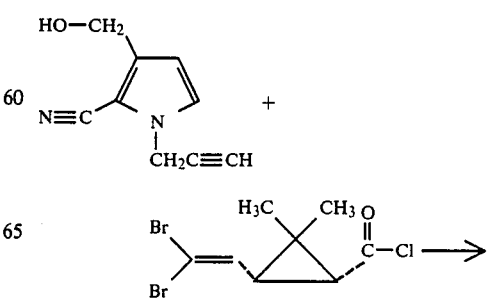

-continued

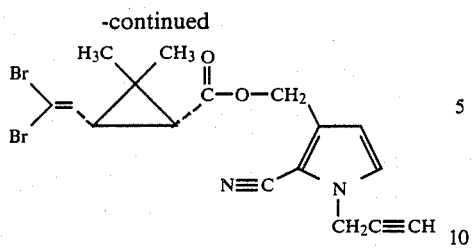

$\alpha_D = -5.5° \pm 1°$ (c=1% in toluene)

EXAMPLE 27

[1-( 2-propynyl)-1H-pyrrol-3-yl]-methyl (1R,cisΔE) 2,2-dimethyl-3-(3-ethoxy-3-oxo-2-fluoro-1-propenyl)-cyclopropane-carboxylate Using the procedure of Example 1, the following reaction was effected to prepare the above compound.

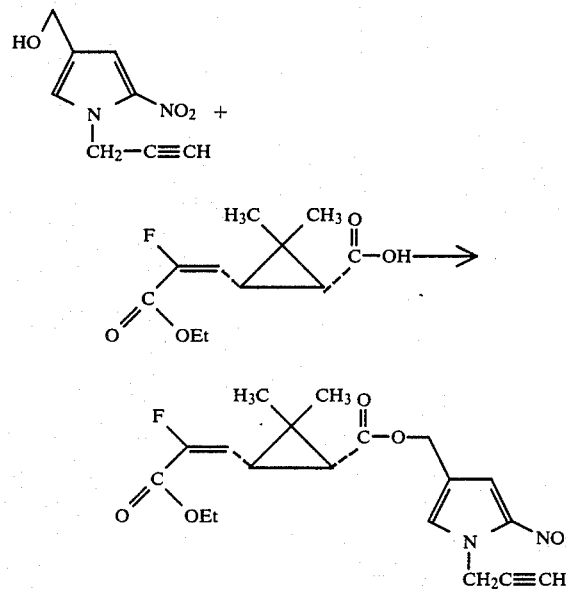

$\alpha_D = +30° \pm 2°$ (c=0.5% in toluene)

EXAMPLE 28

[1-(2-propynyl)-2-nitro-1H-pyrrol-4-yl]-methyl (1R,cis) 2,2-dimethyl-3-(2,2-dibromoethenyl)-cyclopropane carboxylate Using the procedure of Example 1, the following reaction was effected to obtain the above compound.

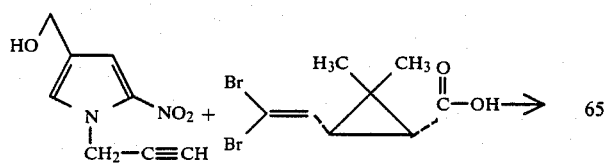

-continued

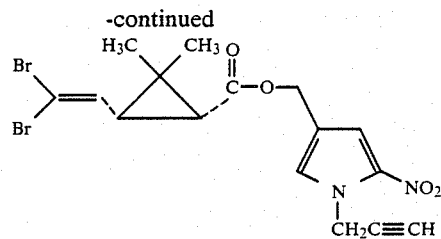

$\alpha_D = -1.5° \pm 1°$ (c=1% in toluene)

EXAMPLE 29

[2-nitro-1-(2-propynyl)-1H-pyrrol-4-yl] (1R,cisΔZ) 2,2-dimethyl-3-(3-methoxy-3-oxo-1-propenyl)-cyclopropane carboxylate

STEP A:

2-nitro-1-(2-propynyl)-1H-pyrrole-4-methanol

At +5° C., 310 mg of sodium hydride at 50% in oil were added to a solution of 0.9 g of 2-nitro-1H-pyrrol-4-carboxaldehyde [prepared by the process described in Bull. Soc. Shim. France p. 283–291 (1972)] and 15 ml of tetrahydrofuran. After allowing the mixture to return to ambient temperature, 0.53 ml of propargyl bromide were added. The reaction mixture was stirred for 6 hours at 60° C., then for 18 hours at 20° C. After filtering and concentrating to dryness, 1 g of residue was obtained which was chromatographed over silica. Elution with a mixture of heptane and ethyl acetate (1-1) yielded 450 mg of product melting at 128° C.

270 mg of potassium borohydride were added to a solution of 450 mg of the said product, 30 ml of tetrahydrofuran and 4 ml of water. After stirring for 15 minutes the mixture was poured into a saturated aqueous solution of sodium chloride, and was extracted with ethyl acetate. The extracts were dried and concentrated to obtain 455 mg of 2-nitro-1-(2-propynyl)-1H-pyrrole-4-methanol.

STEP B: 2-nitro-1-(2-propynyl)-1H-pyrrole-4-yl (1R,cis, ΔZ) 2,2-dimethyl-3-(3-methoxy-3-oxo-1-propenyl)-cyclopropane carboxylate Using the procedure of Example 1, the following reaction was effected to obtain the above compound.

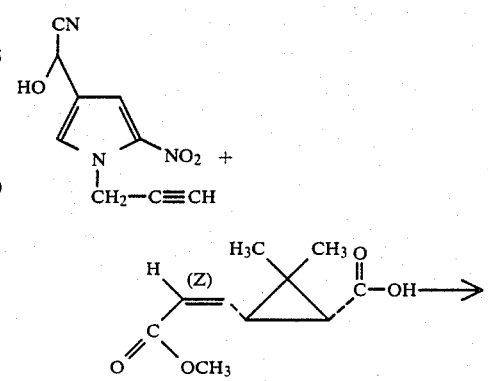

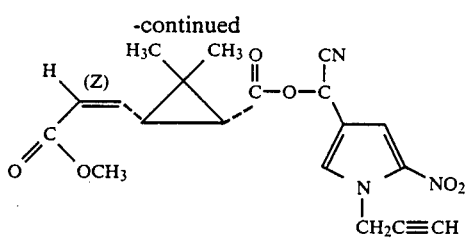

$\alpha D = +57° \pm 2°$ (c=0.5% in toluene)

EXAMPLE 30

[2-nitro-1-(2-propynyl)-1H-pyrrol-4-yl]-methyl (1R,cis,ΔE) 2,2-dimethyl-3-(3-tertbutoxy-3-oxo-2-fluoro-1-propenyl)-cyclopropane carboxylate Using the procedure of Example 1, the following reaction was effected to obtain the above compound.

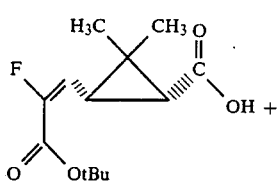

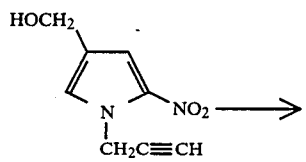

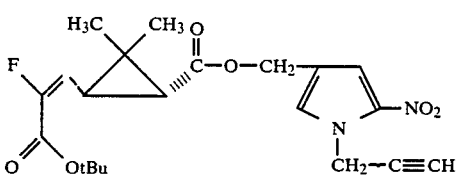

$\alpha_D = 42° \pm 2°$ (c=0.5% in toluene)

EXAMPLE 31

(R,S)-cyano-[2-nitro-1-(2-propynyl)-1H-pyrrol-4-yl]-methyl (1R,cis) 2,2-dimethyl-3-(2,2-dibromoethenyl)-cyclopropane carboxylate

STEP A:

α-hydroxy-1-(2-propynyl)-1H-pyrrole-5-nitro-3-acetonitrile 801 mg of 2-nitro-1-(2-propynyl)-1H-pyrrol-4-carboxaldehyde, 15 ml of methanol and 3 ml of water were mixed together and then 3.6 ml of acetic acid were added. The mixture was cooled to +5° C. and 2.2 g of sodium cyanide were added. The temperature was allowed to return to 20° C. over 4 hours and the reaction mixture was then poured into iced water and extracted with ethyl ether. The ether phase was washed with water, dried and concentrated to obtain 920 mg of α-hydroxy-1-(2-propynyl)-1H-pyrrole-5-nitro-3-acetonitrile.

STEP B: (R,S)

cyano-[2-nitro-1-(2-propynyl)-1H-pyrrol-4-yl]-methyl (1R,cis) 2,2-dimethyl-3-(2,2-dibromoethenyl)-cyclopropane carboxylate Using the procedure of Example 1, the following reaction was effected to obtain the above compound,

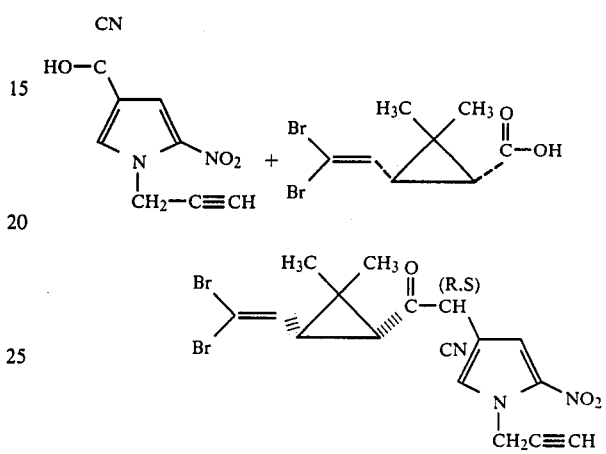

$\alpha D = +26.5° \pm 2°$ (c=0.5% toluene)

EXAMPLE 32

(R,S)-cyano-[2-nitro-1-(2-propynyl)-1H-pyrrol-4-yl]-methyl (1R,cisΔE) 2,2-dimethyl-3-(3-ethoxy-3-oxo-2-fluoro-1-propenyl)-cyclopropane carboxylate Using the procedure of Example 1, the following reaction was effected to obtain the above compound.

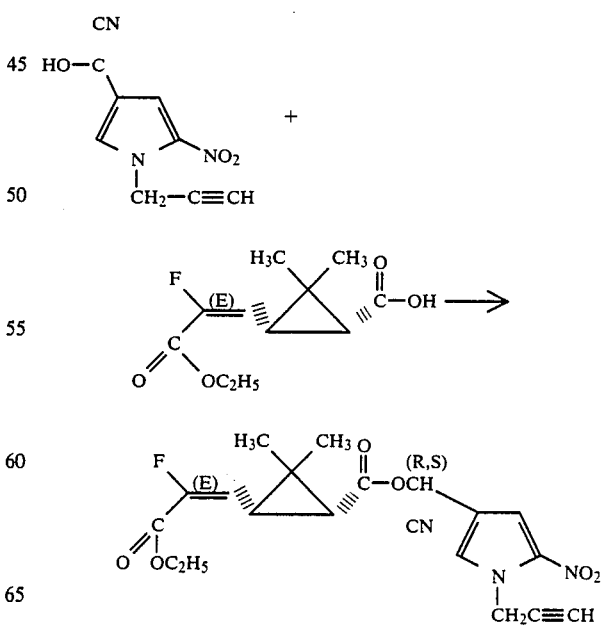

$\alpha_D = +42° \pm 5°$ (c=0.2% toluene)

EXAMPLE 33

[3-nitro-1-(2-propynyl)-1H-pyrrol-4-yl]-methyl (1R,cis) 2,2-dimethyl-3-(2,2-dibromoethenyl)-cyclopropane carboxylate

STEP A:
3-nitro-2-(2-propynyl)-1H-pyrrol-4-carboxaldehyde 826 mg of 3-nitro-1H-pyrrole-4-carboxaldehyde [prepared by the process in Bull. Soc. Chim. p. 283-29 (1972)] were poured into 40 ml of tetrahydrofuran and then, at +5° C., 280 mg of sodium hydride as 50% in oil were added. After leaving the temperature at 20° C. for one hour, 1.19 g of propargyl bromide were added. The mixture was stirred for 18 hours at 20° C. and then was filtered and concentrated. The residue was chromatographed over silica and eluted with a mixture of hexane and ethyl acetate (1-1) to obtain 800 mg of 3-nitro-1-(2-propynyl) 1H-pyrrol-4-carboxaldehyde melting at 120° C.

STEP B: 3-nitro-1-(2-propynyl)-1H-pyrrole-4-methanol

At 20° C., 242 mg of potassium borohydride were introduced into a solution of 400 mg of the product of Step A, 30 ml of tetrahydrofuran and 4 ml of water and the mixture was stirred for 15 minutes at ambient temperature. 10 ml of a saturated aqueous solution of sodium chloride were added with stirring for 5 minutes at 20° C. and after extracting with ethyl acetate, drying and concentrating, 410 mg of 3-nitro-1-(2-propynyl)-1H-pyrrole-4-methanol were obtained melting at 60° C.

STEP C:
[3-nitro-1-(2-propynyl)-1H-pyrrol-4-yl]-methyl (1R,cis) 2,2-dimethyl-3-(2,2-dibromoethenyl)-cyclopropane carboxylate Using the procedure of Example 1, the following reaction was effected to prepare the above compound,

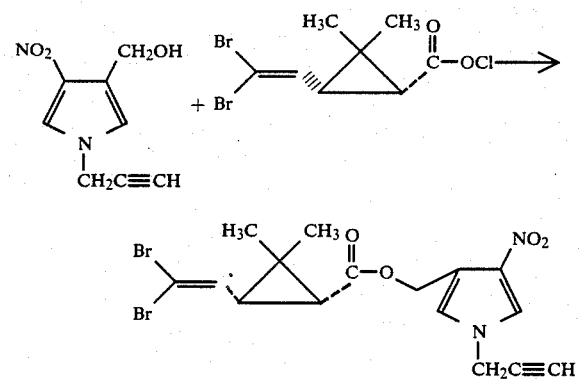

$\alpha_D = -26.5° \pm 2°$ (c=0.5% toluene)

EXAMPLE 34

(R,S)-cyano-[3-nitro-1-(2-propynyl)-1H-pyrrol-4-yl]-methyl (1R,cis) 2,2-dimethyl-3-(2,2-dibromoethenyl)-cyclopropane carboxylate Using the procedure of Example 1, the following reaction was effected to obtain the above compound,

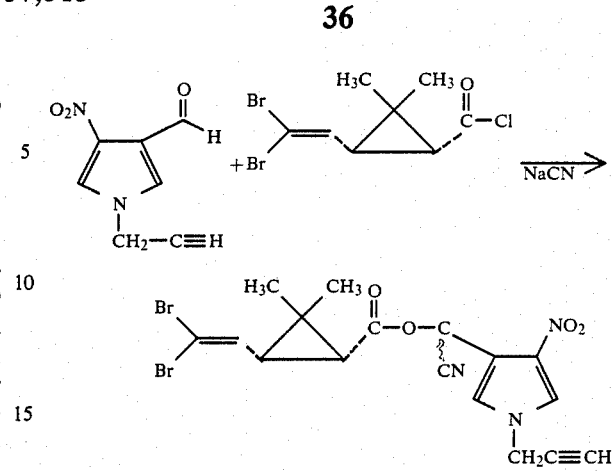

$\alpha_D = -28.5° \pm 1°$ (C=1.3% toluene)

EXAMPLE 35

[(1-propadien)-1H-pyrrol-3-yl]-methyl (1R,cisΔE) 2,2-dimethyl-3-(3-ethoxy-3-oxo-2-fluoro-1-propenyl)-cyclopropane carboxylate

STEP A: 1-propadienyl-1H-pyrrole-3-carboxaldehyde 1 g of pyrrole-3-carboxaldehyde was dissolved in 25 ml of tetrahydrofuran with stirring at the ambient temperature for 15 minutes and after cooling to 0° to 5° C., 528 mg of sodium hydride as 50% in oil were added with stirring for 10 minutes cold. The temperature was allowed to return to the ambient with stirring for 40 minutes under nitrogen and 1 ml of propargyl bromide was added with stirring for a further 2 hours at 40° to 50° C. Then, the reaction mixture was poured into 15 ml of water, and was extracted with methylene chloride. The extracts were dried and concentrated by distilling off the solvent. The residue was chromatographed over silica and eluted with a mixture of hexane and ethyl acetate (7-3) to obtain 1.166 g of 1-propadienyl-1H-pyrrole-3-carboxaldehyde.

STEP B: 3-(1-(propadiene)-pyrrolyl)-methanol 1.009 g of the product of Step A were dissolved in a solution containing 35 ml of tetrahydrofuran and 6.7 ml of water and after stirring for 15 minutes at 20° C., 523 mg of potassium borohydride were added with stirring at 20° C. for 135 minutes. Then the mixture was poured into a saturated aqueous solution of sodium chloride and the mixture was extracted with methylene chloride. The organic phase was dried and concentrated to obtain 0.899 g of 3-(1-(propadiene)-pyrrolyl)-methanol which was utilized as is.

STEP C: [(1-propadien)-1H-pyrrol-3-yl]-methyl (1R,cisΔE) 2,2-dimethyl-3-(3-ethoxy-3-oxo-2-fluoro-1-propenyl)-cyclopropane carboxylate Using the procedure of Example 1, the following reaction was effected to obtain the above compound,

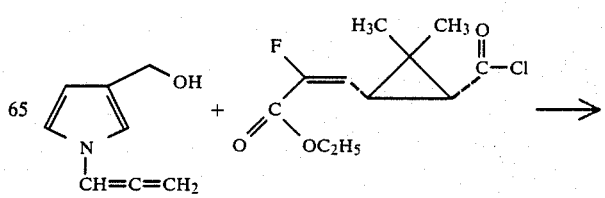

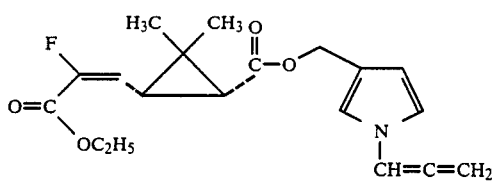

$\alpha_D = +17° \pm 1°$ (c=0.8% toluene)

EXAMPLE 36

[(1-propadien)-1H-pyrrol-3-yl]-methyl (1R,cis) 2,2-dimethyl-3,3-dibromoethenyl-cyclopropane carboxylate Using the procedure of Example 1, the following reaction was effected to obtain the above compound,

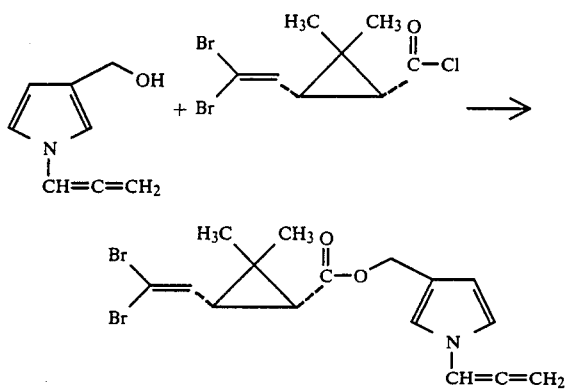

$\alpha_D = -13.5° + 1°$ (c=1% toluene)

EXAMPLE 37

[1-(2-propynyl)-2-trifluoromethyl-1H-pyrrol-3-yl]-methyl (1R,cis) 2,2-dimethyl-3-(2,2-dibromo-ethenyl)-cyclopropane carboxylate

STEP A: ethyl 1-(2-propynyl)-2-trifluoromethyl-3-pyrrole-carboxylate

At 10° C. 1.8 ml of ethyl 3-oxo-4,4,4-trifluorobutanoate were introduced into 3.15 ml of 2-propynylamine in 10 ml of water and after stirring for 10 minutes, 1.65 ml of 1,2-dibromoethyl acetate were added. The mixture was heated at 70° C. for 45 minutes and then was extracted with ethyl acetate. After drying and concentrating the extracts, 6 g of oil were obtained which was chromatographed over silica to obtain 360 mg of ethyl 1-(2-propynyl)-2-trifluoromethyl-3-pyrrole-carboxylate.

STEP B: 1-(2-propynyl)-2-trifluoromethyl-3-pyrrole-methanol

At 5° C., a solution of 1.74 g of the product of Step A in 10 ml of tetrahydrofuran and 270 mg of aluminum lithium hydride were mixed together and the mixture was stirred at ambient temperature for 3 hours and then cooled. 10 ml of ethyl acetate were added with a few drops of a saturated solution of potassium and sodium tartrate. After separating and concentrating cold, 2.4 g of an oil were obtained which were chromatographed over silica. Elution with a cyclohexane-ethyl acetate mixture (8-2) yielded 40 mg of 1-(2-propynyl)-2-trifluoromethyl-3-pyrrole-methanol which melted at 63° C.

STEP C: [1-(2-propynyl)-2-trifluoromethyl-1H-pyrrol-3-yl]-methyl (1R,cis) 2,2-dimethyl-3-(2,2-dibromoethenyl)-cyclopropane carboxylate Using the procedure of Example 1, the following reaction was effected to obtain the above compound,

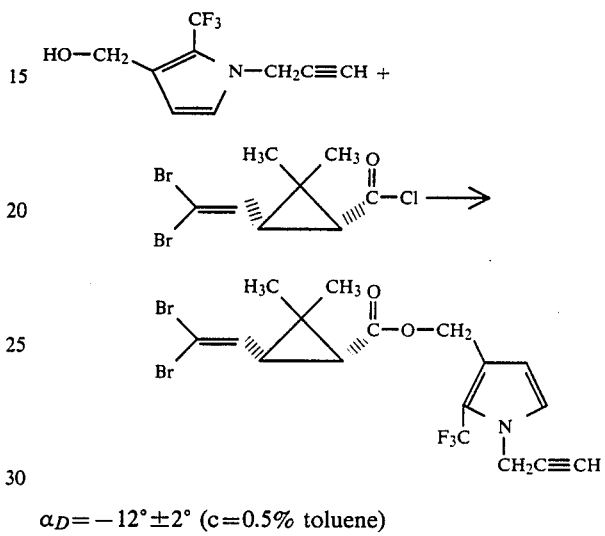

$\alpha_D = -12° \pm 2°$ (c=0.5% toluene)

EXAMPLE 38

[1-(2-propynyl)-2-trifluoromethyl-1H-pyrrol-3-yl]-methyl (1R,cisΔE) 2,2-dimethyl-3-[3-ethoxy-3-oxo-2-fluoro-1-propenyl]-cyclopropane carboxylate Using the procedure of Example 1, the following reaction was effected to obtain the above compound,

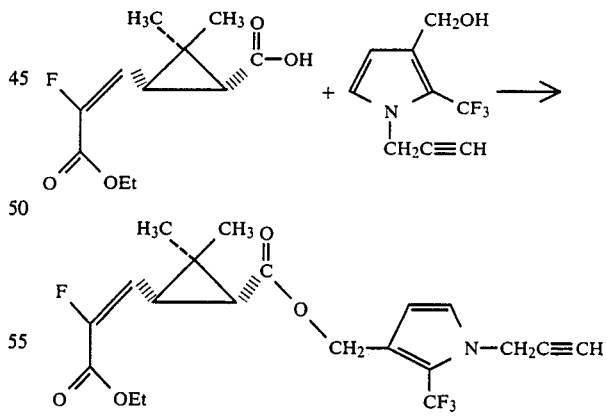

$\alpha_D = +1° \pm 1°$ (c=0.5% of toluene)

EXAMPLE 39

(R,S)-cyano-/1-(2-(propynyl-2-cyano-1H-pyrrol-3-yl/-methyl (1R,cis) 2,2-dimethyl-3-(2,2-dibromo-ethenyl)-cyclopropane carboxylate Using the procedure of Example 1, the following reaction was effected to obtain the above compound,

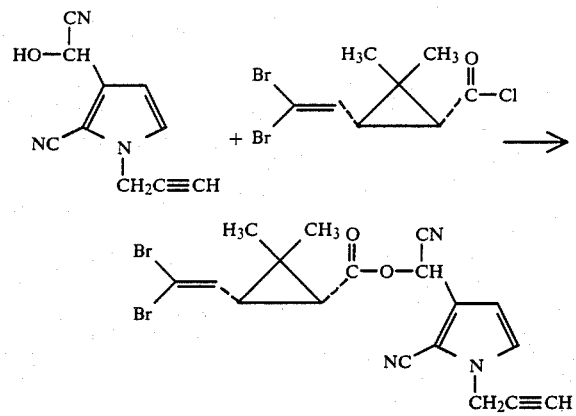

EXAMPLE 40

[2-trifluoromethyl-1-(2-propynyl)-1H-pyrrol-3-yl]-methyl (1R,cis,ΔE) 2,2-dimethyl-3-(3-tertbutyloxy-3-oxo-2-fluoropenyl)-cyclopropane carboxylate A solution of 455 mg of dicyclohexylcarbodiimide, 3 mg of 4-dimethylamino-pyridine and 5 ml of anhydrous methylene chloride was added dropwise to a mixture, cooled in an ice bath, of 450 mg of 1-(2-propynyl)-2-trifluoromethyl-3-pyrrole methanol, 570 mg of (1R,cisΔE) 2,2-dimethyl-3-(3-tertbutoxy-3-oxo-2-fluoro-1-propenyl)-cyclopropane carboxylic acid and 4 ml of anhydrous methylene chloride. The reaction mixture was allowed to return to ambient temperature and was stirred for 5 hours. The precipitate formed was eliminated by filtration and the filtrate was taken up in isopropyl ether and concentrated. The insoluble matter was filtered off and the filtrate was concentrated. The residue was chromatographed over silica and eluted with a mixture of hexane and ethyl acetate (9–1) to obtain 518 mg of [2-trifluoromethyl-1-(2-propynyl)-1H-pyrrol-3-yl]-methyl (1R,cisΔE) 2,2-dimethyl-3-(3-tert-butyloxy-3-oxo-2-fluorophenyl)-cyclopropane carboxylate.

EXAMPLE 41

[2-trifluoromethyl-1-(2-propynyl)-1H-pyrrol-3-yl]-methyl (1R,cis) 2,2-dimethyl-3-ethenyl-cyclopropane carboxylate Using the procedure of Example 1, 610 mg of (1R,cis) 2,2-dimethyl-3-ethenyl-cyclopropane carboxylic acid and with 800 mg of 1-(2-propynyl)-2-trifluromethyl-3-pyrrole-methanol were reacted to obtain 1.28 g of [2-trifluoromethyl-1-(2-propynyl)-1H-pyrrol-3-yl]-methyl (1R,cis) 2,2-dimethyl-3-ethenyl-cyclopropane carboxylate with a specific rotation of $[\alpha]_D = +9°$ (0.2% toluene)

EXAMPLE 42

[2-trifluoromethyl-1-(2-propynyl)-1H-pyrrol-3-yl]-methyl (1R,cisΔZ) 2,2-dimethyl-3-[3-methoxy-(3-oxo-1-propenyl)]-cyclopropane carboxylate Using the procedure of Example 1, 860 mg (1R,cisΔZ) 2,2-dimethyl-3-(3-methoxy-3-oxo)-1-propenyl-cyclopropane carboxylic acid and 800 mg of 1-(2-propynyl)-2-trifluoromethyl-3-pyrrole-methanol were reacted to obtain 1.18 g of [2-trifluoromethyl-1-(2-propynyl)-1H-pyrrol-3-yl]-methyl (1R,cisΔZ) 2,2-dimethyl-3-[3-methoxy-(3-oxo-1-propenyl)]-cyclopropane carboxylate with a specific rotation of $[\alpha]_D = +17.5°$ (0.7% toluene)

EXAMPLE 43

[2-cyano-1-(2-propynyl)-1H-pyrrol-3-yl]-methyl (1R,cisΔZ) 2,2-dimethyl-3-[(2-chloro-3,3,3-trifluoro)-1-propenyl]-cyclopropane carboxylate 430 mg of [2-cyano-1-(2-propynyl)-1H-pyrrole]-3-methanol and 600 mg of (1R,cisΔZ) 2,2-dimethyl-3-[2-chloro-3,3,3-trifluoro)-1-propenyl]-cyclopropane carboxylic acid were introduced into 12 ml of methylene chloride and at 0° C., a solution of 509 mg of dicyclohexylcarboxiimide and 3 mg of dimethylamino-pyridine in 2 ml of methylene chloride was added dropwise to the solution obtained. The mixture was stirred for 5 hours at 20° C. and then filtered. The filtrate was concentrated to dryness and isopropyl ether was added. The residual insoluble matter was eliminated by filtering and the filtrate was concentrated to dryness. A mixture of hexane and isopropyl ether (1–1) was added, followed by filtering and concentrating the filtrate to dryness. The residue was chromatographed over silica and eluted with a mixture of hexane and isopropyl ether (1–1), and to the product obtained, which still contains a little urea, 2 ml of isopropyl ether were added. The isoluble matter formed was eliminated by filtering, and then the filtrate was concentrated to dryness by distilling under reduced pressure to obtain 896 mg of [2-cyano-1-(2-propynyl)-1H-pyrrol-3-yl]-methyl (1R,cisΔZ) 2,2-dimethyl-3-[(2-chloro-3,3,3-trifluoro)-1-propenyl]-cyclopropane carboxylate with a specific rotation of $[\alpha]_D = +7°$ (c=0.4% toluene)

Analysis: $C_{18}H_{16}ClF_3N_2O_2$: molecular weight=884,789 Calculated: %C 56.19; %H 4.19; %Cl 9.21; %F 14.8; %N 7.28; Found: %C 56.3; %H 4.4; %Cl 9.0; %F 14.9; %N 7.2.

EXAMPLE 44 cyano-[1-(2-propynyl)-1H-pyrrol-3-yl]-methyl (1R,cisΔE) 2,2-dimethyl-3-(3-ethoxy-2-fluoro-3-oxo-1-propenyl)-cyclopropane carboxylate

STEP A:

4-hydroxy-1-(2-propynyl)-1H-pyrrole-5-cyano-3-acetonitrile 6 g. of 1-(2-propynyl)-1H-pyrrole-2-carbonitrile, 125 ml of methanol and 25 ml of water were mixed together and after cooling to +5° C. 15.2 ml of acetic acid were added, followed by 9.3 g of sodium cyanide in several lots. The temperature was allowed to rise to 20° C. over 4 hours and the mixture was poured into a liter of water and extracted with ethyl ether. The organic phases were dried and concentrated to dryness to obtain 7 g of 4-hydroxy-1-(2-propynyl)-1H-pyrrole-5-cyano-3-acetonitrile melting at 60° C.

STEP B: cyano-[1-(2-propynyl)-1H-pyrrol-3-yl]-methyl (1R,cisΔE) 2,2-dimethyl-3-(3-ethoxy-2-fluoro-3-oxo-1-propenyl)-cyclopropane carboxylate 2 g of (R,S) cyano-[2-cyano-1-(2-propynyl)-1H-pyrrol-3-yl]-4-methanol and 2.48 g of (1R,cisΔE) 2,2-dimethyl-3-(3-(3-ethoxy-2-fluoro-3-oxo-1-propenyl)-cyclopropane carboxylic acid were dissolved in 30 ml of methylene chloride and then, at +10° C. and over about 30 minutes, a solution of 2.22 g of dicyclohexylcarboxiimide and of 13 mg of 4-dimethylamino-pyridine in 30 ml of methylene chloride was added. The mixture was stirred for 18 hours at 20° C. and after filtering, the filtrate was concentrated to dryness. Ethyl ether was added and the mixture was filtered and concentrated to dryness again. The residue was chromatographed over silica and eluted with a mixture of hexane and ethyl acetate (7–3) to obtain 3.14 g of cyano-[1-(2-propynyl)-1H-pyrrol-3-yl]-methyl (1R,cisΔE) 2,2-dimethyl-3-(3-ethoxy-2-fluoro-3-oxo-1-propenyl)-cyclopropane carboxylate with a specific rotation of $[\alpha]_D = +40°$ C. (c=1% toluene).

EXAMPLE 45

[1-(2-propynyl)-3-trifluoromethyl)-1H-pyrrol-4-yl]methyl (1R,cisΔE) 2,2-dimethyl-3-[2-fluoro-3-oxo-3-tertbutoxypropenyl]-cyclopropane carboxylate

STEP A: ethyl 3-trifluoromethyl-1H-pyrrol-4-carboxylate 7.4 g of ethyl 4,4,4-trifluoro-(E)-butenoate (E. T. McBee, J. Am. Soc. Vol. 76 p. 3724 (1924)) and 8.6 g of tosylmethyl isocyanide were introduced into 200 ml of a mixture of dimethylsulfoxide and ethyl ether (1–2) and then 2.9 g of sodium hydride at 50% in vaseline were added in small portions. Hydrogen evolved and after stirring for 30 minutes at 20° C., a few drops of acetic acid were added. The mixture was poured into a mixture of water and ice and was extracted with ether. The extracts were concentrated to dryness by distilling under reduced pressure and the residue was chromatographed over silica. Eluting with a mixture of hexane and ethyl acetate (7–3) to yielded 6.6 g of ethyl 3-trifluoromethyl-1H-pyrrol-4-carboxylate melting at 165° C.

Analysis: $C_8H_8F_3NO_2$: molecular weight=207.154
Calculated: %C 46.39; %H 3.85; %F 27.51; %N 6.76;
Found: %C 46.5; %H 3.9; %F 27.1; %N 6.8.

STEP B: ethyl 1-(2-propynyl)-3-trifluoromethyl-1H-pyrrole-4-carboxylate 1 g of ethyl 3-trifluoromethyl-1H-pyrrole-4-carboxylate of Step A was introduced into 10 ml of tetrahydrofuran, followed, at 0° C. by 240 mg of sodium hydride at 50% in vaseline oil in small portions. After stirring for 30 minutes at 20° C. and cooling to 0° C., a solution of 0.45 ml of propargyl bromide in 1 ml of tetrahydrofuran was added with stirring for 30 minutes at 0° C., then for 1 hour at 20° C., followed by cooling again to 0° C. A little sodium hydride was added then 0.45 ml of propargyl bromide in solution in 1 ml of tetrahydrofuran with stirring at 0° C. The mixture was poured into water and extracted with methylene chloride. The extracts were concentrated to dryness by distilling under reduced pressure and the residue was chromatographed over silica. Elution with a mixture of hexane and ethyl acetate (8–2) yielded 0.950 g of ethyl 1-(2-propynyl)-3-trifluoromethyl-1H-pyrrole-4-carboxylate melting at 58° C.

STEP C: 1-(2-propynyl)-3-trifluoromethyl-1H-pyrrole-4-methanol

At 0° C., 1.95 g of lithium aluminium hydride were introduced in small portions into a solution of 12.6 g of ethyl 1-(2-propynyl)-3-trifluoromethyl-1H-pyrrole-4-carboxylate in 65 ml of tetrahydrofuran with stirring for 2 hours at 20° C. 10 ml of ethyl acetate were added to eliminate possible excess of hydride and the reaction mixture was poured into a saturated solution of sodium-potassium double tartrate. After extraction with ethyl acetate, the extracts were concentrated to dryness by distillation under reduced pressure. The residue was chromatographed over silica and eluted with a mixture of hexane and ethyl acetate (7–3) to obtain 5.7 g of 1-(2-propynyl)-3-trifluoromethyl-1H-pyrrole-4-methanol melting at 45° C.

STEP D: [1-(2-pyropynyl)-3-trifluoromethyl-1H-pyrrol-4-yl]-methyl (1R,cisΔE) 2,2-dimethyl-3-[2-fluoro-3-oxo-3-tert.-butoxypropenyl)-cyclopropane carboxylate 1 g of 1-(2-propynyl)-3-trifluoromethyl-1H-pyrrole-4-methanol and 1.5 g of (1R,cisΔE) 2,2-dimethyl-3-[2-fluoro-3-oxo-3-tert-butoxypropenyl]-cyclopropane carboxylic acid were dissolved in 25 ml of methylene chloride and then, at 0° C., a mixture of 1.3 g of dicyclohexylcarbodiimide and 150 mg of 4-dimethylamino-pyridine in methylene chloride was introduced progressively. The mixture was stirred for 15 minutes at 0° C. and then for 2 hours at 20° C. and was then filtered. The filtrate was concentrated to dryness and isopropyl ether was added, after which the temperature was reduced to 0° C. Then by filtering, concentrating to dryness by distilling under reduced pressure, chromatographing the residue twice on silica and eluting with a mixture of hexane and ethyl acetate (35–15), 1.7 g of [1-(2-pyropynyl)-3-trifluoromethyl-1H-pyrrol-4-yl]-methyl (1R,cisΔE) 2,2-dimethyl-3-[2-fluoro-3-oxo-3-tert.-butoxypropynyl)-cyclopropane carboxylate were obtained with a specific rotation of $[\alpha]_D = 40.5°$ (c=0.7% in chloroform)

Analysis: $C_{22}H_{25}F_4NO_4$: molecular weight=443.443
Calculated: %C 59.6; %H 5.68; %F 17.14; %N 3.16;
Found: %C 59.2; %H 5.7; %F 17.1; %N 3.2.

EXAMPLE 46

(R,S)-cyano-[(1-benzoyl)-1H-pyrrol-3-yl]-methyl (1R,cis) 2,2-dimethyl-3-(2,2-dibromoethenyl)-cyclopropane carboxylate

STEP A: 1-benzoyl-3-formyl-pyrrole 500 mg of 3-formyl-pyrrole were dissolved in 10 ml of tetrahydrofuran and then, at +20° C., 227 mg of sodium hydride dispersed at 55% in vaseline oil were added all at once. Gas evolved and after stirring for 15 minutes, a solution of 0.58 ml of benzoyl chloride in 2 ml of tetrahydrofuran was introduced dropwise at +5° C. The mixture was stirred for 2 hours at 20° C. and diluted with water. Extracting with ether, concentrating to dryness by distillation under reduced pressure and chromatographing the residue over silica and eluting with a mixture of hexane and ethyl acetate (7–3) yielded 558 mg of 1-benzoyl-3-formyl-pyrrole.

NMR Spectrum (deuterochloroform)
Peaks from 6.8 to 6.9 ppm (4-hydrogen of pyrrole);
Peak at 7.4 ppm (5-hydrogen of pyrrole);
Peaks at 7.5 to 8.0 ppm (hydrogens of phenyl);
Peak at 7.93 ppm (5-hydrogen of pyrrole);
Peak at 10.0 ppm (hydrogen of formyl).

STEP B: α-cyano-3-[(1-benzoyl)-1-pyrrole]-methyl alcohol 0.9 g of 1-benzoyl-3-formyl-pyrrole, 12 ml of methanol, 4 ml of water, 1 ml of acetic acid and 0.47 g of sodium cyanide were mixed together and stirred at +20° C. for 4 hours. The reaction mixture was poured into iced salt water and extracted with ethyl acetate. The extracts were concentrated to dryness by distillation under reduced pressure. The residue was chromatographed over silica and eluted with a mixture of hexane and ethyl actate (1-1) to obtain 0.57 g of α-cyano-3-[(1-benzoyl)-1-pyrrole]-methyl alcohol melting at 85° C.

NMR Spectrum (deuterochloroform)
Peak at 5.5 ppm (hydrogen of

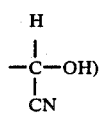

Peak at 6.5 ppm (4-hydrogen of pyrrole);
Peaks from 7.3 to 7.9 ppm (hydrogens of phenyl).

STEP C: (R,S) cyano-[(1-benzyl)-1H-pyrrol-3-yl]-methyl (1R,cis) 2,2-dimethyl-3-(2,2-dibromoethenyl)-cyclopropane carboxylate The following reaction was effected to produce the above named compound.

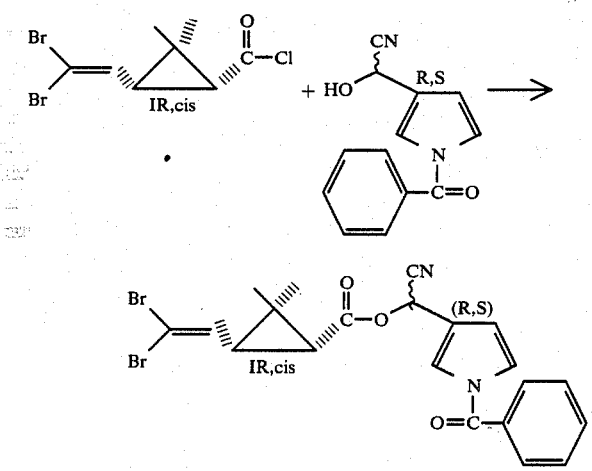

CCM=Rf=0.5 (hexane-ethyl acetate 7-3)

EXAMPLE 47

[1-(2-propynyl-2-methoxy-2-oxo-1H-pyrrol-3-yl]-methyl (1R,cis) 2,2-dimethyl-3-(2,2-dibromoethenyl)-cyclopropane carboxylate

STEP A: methyl 1H-pyrrole-2-carboxylate 40 ml of a solution of 45 (mmoles) of 2-chlorocarbonyl-1H-pyrrole in methylene chloride were added dropwise to a cold mixture of 4.3 ml of pyridine and 3.5 ml of methanol and the mixture was washed with water, then with 6 ml of N sodium hydroxide, and was extracted with methylene chloride. The organic phases were dried and concentrated to dryness and the residue was chromatographed over silica. Elution with a mixture of hexane and ethyl acetate (8-2) yielded 4.014 g of methyl 1H-pyrrole-2-carboxylate melting at ≃74° C.

STEP B: methyl 1-(2-propynyl)-1H-pyrrol-2-carboxylate 3.302 g of methyl 1H-pyrrole-2-carboxylate were dissolved in 40 ml of tetrahydrofuran and then, at 0° C., 1.422 g of sodium hydride in suspension at 50% in vaseline oil were added. The mixture stirred for 1 hour at 20° C. and a solution of 2 ml of propargyl bromide in 10 ml of tetrahydrofuran was introduced dropwise. The mixture was stirred for 1 hour at 50° C. and after having added 5 ml of propargyl bromide, the reaction mixture was poured into water. The mixture was extracted with methylene chloride and the extracts were concentrated to dryness by distilling under reduced pressure. The residue was chromatographed over silica and eluted with a mixture of hexane and ethyl acetate (9-1) to obtain 2.993 g of methyl 1-(2-propynyl)-1H-pyrrol-2-carboxylate.

NMR Spectrum (deuterochloroform)
Peaks at 2.37-2.42-2.46 ppm (hydrogen of —H—C≡CH);
Peak at 3.8 ppm (hydrogens of —OCH₃);
Peaks at 5.16-5.20 ppm (hydrogens of —CH₂—C≡CH—C);
Peaks from 6.1 to 6.2 ppm(2-hydrogen of pyrrole);
Peaks from 6.9 to 7.0 ppm and from 7.1 to 7.2 ppm (3- and 5-hydrogens of pyrrole).

STEP C: methyl 4-formyl-1-(2-propynyl)-1H-pyrrole-2-carboxylate 2.981 g of methyl 1-(2-propynyl)-1H-pyrrole-2-carboxylate in 11 ml of methylene chloride and 1 ml of nitromethane in 4 ml of methylene chloride were mixed together to obtain solution A. 4.312 g of aluminium chloride were suspended in 11 ml of methylene chloride and after cooling to −62° C., solution A was added dropwise. Then a solution of 2.3 ml of dichloromethyl methyl ether and 19 ml of methylene chloride were added and the mixture was stirred for 2 hours at −60° C., then for 1 hour at ambient temperature. 200 ml of methylene chloride and 300 ml of water were added and after neutralizing with 11 ml of 10N sodium hydroxide, stirring and decanting, the organic phase was washed with a solution of potassium bicarbonate, dried and concentrated to dryness. The residue was chromatographed over silica and eluted with a mixture of hexane and ethyl acetate (7-3) to obtain 2.734 g of methyl 4-formyl-1-(2-propynyl)-1H-pyrrole-2-carboxylate.

STEP D: methyl 4-(hydroxymethyl)-1-(2-propynyl)-1H-pyrrole-2-carboxylate 747 mg of methyl 4-formyl-1-(2-pyropynyl(-1H-pyrrole-2-carboxylate were dissolved in 12 ml of tetrahydrofuran and 3.3 ml of water and 426 mg of potassium borohydride were added. The mixture was stirred for 5 hours at 20° C. and was poured into a saturated aqueous solution of sodium chloride and extracted with methylene chloride. The extracts were concentrated to dryness by distilling under reduced pressure to obtain 758 mg of methyl 4-(hydroxymethyl)-1-(2-propynyl)-1H-pyrrole-2-carboxylate melting at 77° C.

IR Spectrum (chloroform)
absorption at 3609 cm⁻¹ (—OH)
absorption at 3307 cm⁻¹ (—C≡CH)

absorption at 2110 cm$^{-1}$ (—C≡C)
absorption at 1702 cm$^{-1}$ (—C=O)
absorption at 1445 cm$^{-1}$ (—CH$_3$)
absorption at 1564, 1476 cm$^{-1}$ (heterocycle).

STEP E:

[1-(2-propynyl-2-methoxy-2-oxo-1H-pyrrol-3-yl]-methyl (1R,cis)
2,2-dimethyl-3-(2,2-dibromoethenyl)-cyclopropane carboxylate The following reaction was effected to obtain the above compound

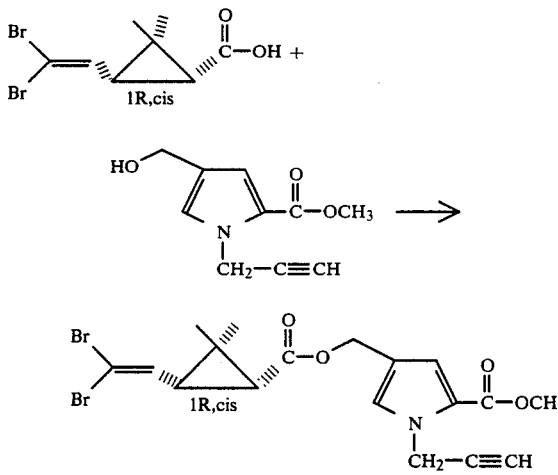

$[\alpha]_D = -6°$ (c=0.5% toluene).

EXAMPLE 48

(R or S)-cyano-[1-(2-propynyl)-2-methoxycarbonyl-1H-pyrrol-3-yl]-methyl (1R,cis)
2,2-dimethyl-3-(2,2-dibromoethenyl)-cyclopropane carboxylate The following reaction was effected to obtain the above named compound

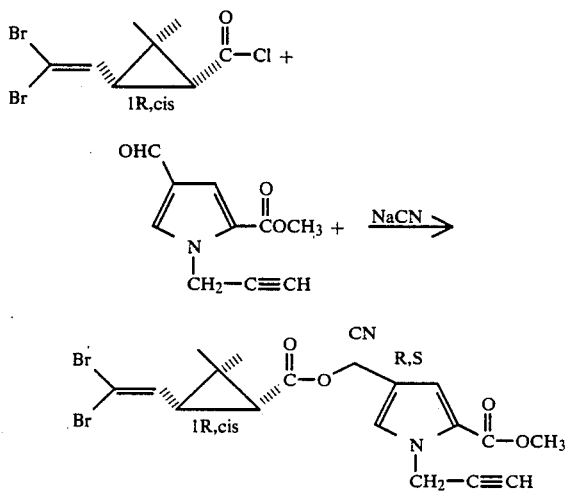

$[\alpha]_D = -36.5°$ (c=0.4%, toluene).

EXAMPLE 49

[1-(2-propynyl)-2-cyano-1H-pyrrol-3-yl]-methyl 1R, trans (E,⅓) (Z,⅔)
2,2-dimethyl-3-(2-chloro-2-trifluoromethylethenyl)-cyclopropane carboxylate The following reaction was effected to obtain the above named compounds

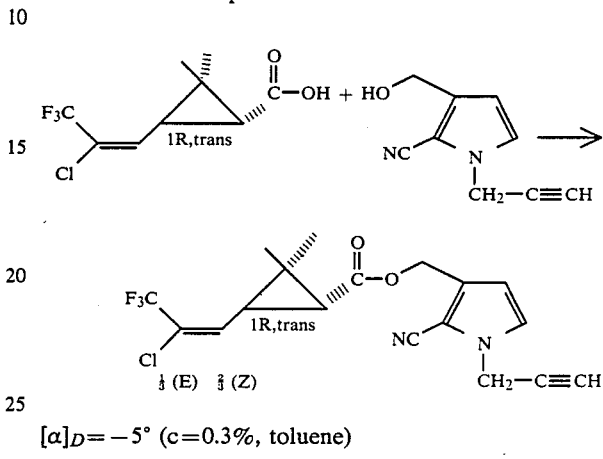

$[\alpha]_D = -5°$ (c=0.3%, toluene)

EXAMPLE 50

(R,S)-cyano-[1-(2-propenyl)-1H-pyrrol-3-yl]methyl (1R,cis)
2,2-dimethyl-3-(2,2-dibromoethenyl)cyclopropane carboxylate 682 mg of (R,S)-cyano[1-(2-propynyl)-1H-pyrrol-3-yl]-methyl (1R,cis) 2,2-dimethyl-3-(2,2-dibromoethenyl)cyclopropane carboxylate and 25 ml of dioxane were mixed together in a hydrogenating apparatus and then 147 mg of palladium at 5% on barium sulfate and 1/10 ml of quinoline were added. After purging and stirring under hydrogen, hydrogenation was stopped when 35 ml of hydrogen had been absorbed. The reaction mixture was filtered on charcoal and the filtrate was concentrated to dryness by distillation under reduced pressure. After chromatographing of the residue and elution with a hexane/ethyl acetate mixture (85–15) with 2% of triethylamine, 535 mg of (R,S)-cyano-[1-(2-propenyl)-1H-pyrrol-3-yl]methyl (1R,cis) 2,2-dimethyl-3-(2,2-dibromoethenyl)cyclopropane carboxylate were obtained melting at 60° C. and $[\alpha]_D = -54°$ (c=0.6% toluene).

EXAMPLE 51

[1-(2-propynyl)-2-cyano-1H-pyrrol-3-yl]methyl (1R,cis)
2,2-dimethyl-3-(3-methoxy-3-oxo-1-propenyl)cyclopropane carboxylate The following reaction was effected to produce the above compound:

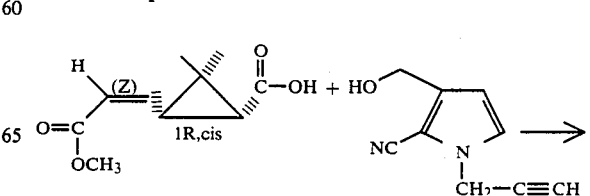

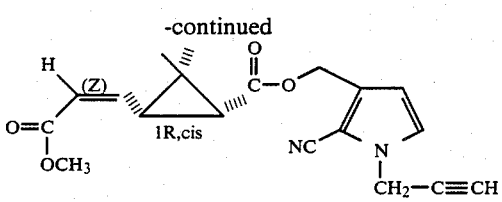

$[\alpha]_D = +39°$ (c=0.6% toluene).

EXAMPLE 52

[1-(2-propynyl)-2-cyano-1H-pyrrol-3-yl]methyl (1R,cis) 2,2-dimethyl-3-(2-fluoro-2-ethoxy-2-oxo-1-propenyl)cyclopropane carboxylate The following reaction was effected to produce the above compound:

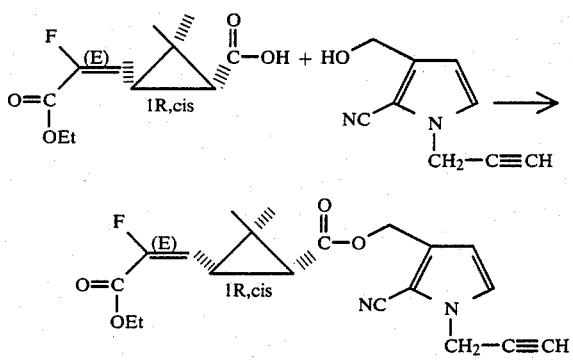

$[\alpha]_D = +18°$ (c=0.4% toluene)

EXAMPLE 53

[1-(2-propenyl)-2-cyano-1H-pyrrol-4-yl]methyl (1R,cisΔE) 2,2-dimethyl-3-[2-fluoro-2-ethoxy-2-oxo-1-propenyl]cyclopropane carboxylate

Step A:
2-cyano-1-(2-propenyl)-1H-pyrrol-4-carboxaldehyde

Into a mixture of 20 g of 2-cyano-4-formyl-1H-pyrrole and 250 ml of tetrahydrofuran, there is added in small portions 8.01 g of a 50% suspension of sodium hydride in vaseline oil, and then, at 20° C., a mixture of 14 ml of allyl bromide and 20 ml of tetrahydrofuran. The mixture was stirred for 2 hours at 60° C., and a further 14 ml of allyl bromide were added. The mixture was stirred for a further 2 hours at 60° C. and was then poured into water and extracted with methylene chloride. The extracts were concentrated to dryness by distilling under reduced pressure and the residue was chromatographed over silica. Elution with a mixture of hexane and ethyl acetate (6-4) yielded 24.1 g of [1-(2-propenyl)-2-cyano-1H-pyrrol-4-yl]methyl (1R,cisΔE) 2,2-dimethyl-3-[2-fluoro-2-ethoxy-2-ox-1-propenyl]cyclopropane carboxylate.

Step B: 2-cyano-1-(2-propenyl)-1H-pyrrole-4-methanol 14.1 g of 4-formyl-2-cyano-1-(2-propenyl)-1H-pyrrol, 160 ml of tetrahydrofuran, and 43 ml of water were mixed together and 481 mg of lithium borohydride were added. The mixture was stirred at 20° C. for 30 minutes and a further 493 mg of lithium borohydride were added. The mixture was stirred at 20° C. for 30 minutes and then ethyl acetate was added. After pouring into a saturated aqueous solution of sodium chloride, extracting with ethyl acetate and concentrating to dryness by distilling under reduced pressure, the residue was chromatographed over silica. Elution with a mixture of hexane and ethyl acetate (55-45) yielded 13.882 g of [1-(2-propenyl)-2-cyano-1H-pyrrol-4-yl]methyl (1R,cisΔE) 2,2-dimethyl-3-[2-fluoro-2-ethoxy-2-oxo-1-propenyl]cyclopropane carboxylate.

NMR Spectrum (dueterochloroform)
peak at 1.97 ppm (hydrogen of —OH);
peak at 4.5 ppm (hydrogens of —CH₂O);
peaks at 4.5–4.7 ppm (hydrogens of —N—CH₂);
peaks from 5.0 to 5.4 ppm (hydrogens of =CH₂);
peaks from 5.7 to 6.2 ppm (hydrogen of —CH=),
peaks at 6.8–6.9 ppm (aromatic hydrogens).

Step C:
[1-(2-propenyl)-2-cyano-1H-pyrrol-4-yl]-methyl (1R,cisΔE) 2,2-dimethyl-3-[2-fluoro-2-ethoxy-2-oxo-1-propenyl]-cyclopropane carboxylate The following reaction was effected to produce the above compound:

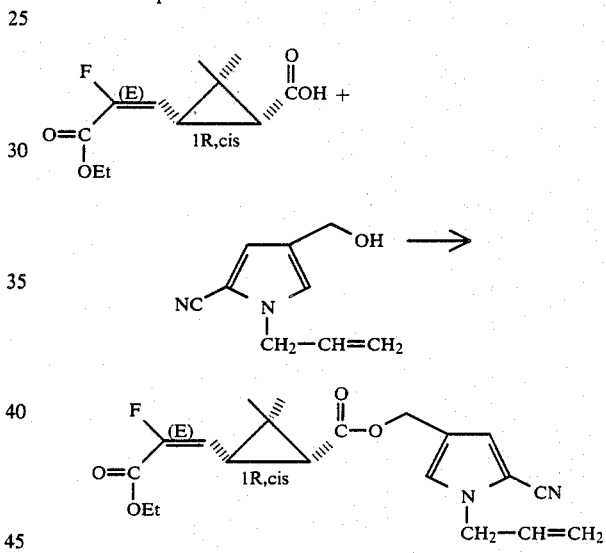

$[\alpha]_D = 25°$ (c=0.7% toluene)

EXAMPLE 54

[1-(2-propenyl)-2-cyano-1H-pyrrol-4-yl]methyl (1R,cis) 2,2-dimethyl-3-(2,2-dibromoethenyl)-cyclopropane carboxylate The following reaction was effected to produce the above compound:

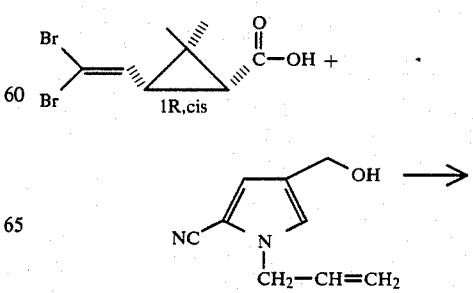

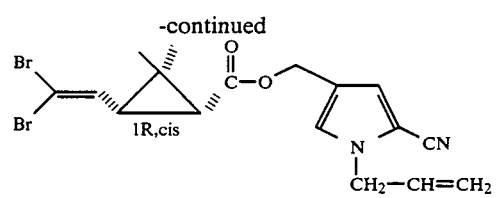

[α]$_D$ = −11.5° (c=0.5% toluene)

EXAMPLE 55

(R,S)-cyano-[1-(2-propenyl)-2-cyano-1H-pyrrol-4-yl]-methyl (1R,cis) 2,2-dimethyl-3-(2,2-dibromoethenyl)-cyclopropane carboxylate 1.072 g of 2-cyano-1-(2-propenyl)-1H-pyrrole-4-carboxaldehyde, 15 ml of methanol, 4.5 ml of water and 2.5 ml of acetic acid were mixed together and then, at 0° C., 2 g of sodium cyanide were added. The mixture was stirred at 20° C. for 4½ hours and then 3 ml of acetic acid and 3 g of sodium cyanide were added. The mixture was stirred for 2 hours at 20° C. and, after washing with water, extracting with methylene chloride, and concentrating to dryness by distilling under reduced pressure, 1.25 g of α-hydroxy-[2-cyano-1-(2-propenyl)]-1H-pyrrole-4-acetonitrile was obtained, which was used as is.

The following reaction was conducted to obtain the above compound:

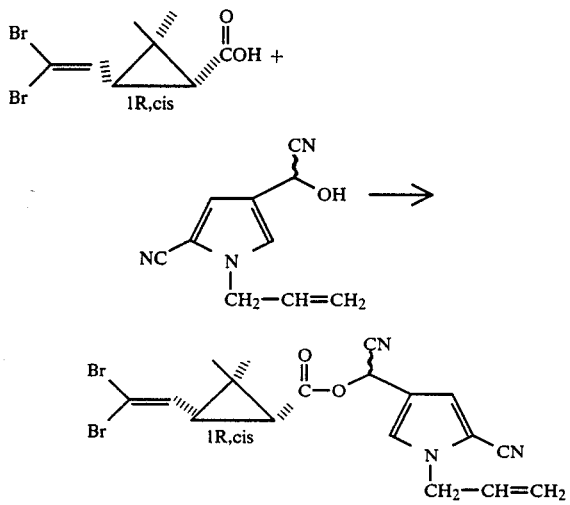

[α]$_D$ = +7° (c=0.5% toluene)

EXAMPLE 56

1-(2-propenyl-1H-pyrrol-3-yl)-methyl (1R,cisΔE) 2,2-dimethyl-3-(2-fluoro-3-ethoxy 3-oxo-1-propenyl)-cyclopropane carboxylate 700 mg of 1-(2-propynyl-1H-pyrrol-3-yl)-methyl (1R,cis,ΔE) 2,2-dimethyl-3-(2-fluoro-3-ethoxycarbonyl-1-propenyl)-cyclopropane carboxylate, 0.14 ml of quinoline and 200 mg of 5% palladium on barium sulfate were introduced into a hydrogenating apparatus and stirred under hydrogen. When 45 ml of hydrogen had been absorbed, the reaction was stopped. After filtering, concentrating the filtrate to dryness by distilling under reduced pressure, and chromatography of the residue over silica and eluting with a mixture of hexane and ethyl acetate (7–3) with 2% of triethylamine, 482 mg of 1-(2-propenyl-1H-pyrrol-3-yl)-methyl (1R,cisΔE) 2,2-dimethyl-3-(2-fluoro-3-ethoxycarbonyl-1-propenyl)-cyclopropane carboxylate were obtained with the specific rotation of [α]$^D$ = +15.5° (c=0.4% toluene).

EXAMPLE 57

[1-(2-propynyl)-2-cyano-1H-pyrrol-4-yl]-propyn-2-yl (1R,cisΔE) 2,2-dimethyl-3-[2-fluoro-3-ethoxy-3-oxo-1-propenyl]-cyclopropane carboxylate

STEP A: 1(R,S) hydroxy-[2-cyano-1-(2-propynyl)-1H-pyrrol-4-yl]-2-propynyl

A solution of 3 g of 1-(2-propynyl)-2-cyano-4-formyl-1H-pyrrole in 20 ml of tetrahydrofuran was introduced at +20° C. over about 10 minutes into 70 ml of a solution of ethynylmagnesium bromide in tetrahydrofuran titrating 0.82 mmole/l. After stirring for 3½ hours, the reaction mixture was poured into a saturated aqueous solution of monosodium phosphate and extracted with ether. The extracts were concentrated to dryness by distilling under reduced pressure and the residue was purified by chromatography over silica. Elution with a mixture of hexane and ethyl acetate (1–1) yielded 2.897 g of 1(R,S) hydroxy-[2-cyano-1-(2-propynyl)-1H-pyrrol-4-yl]-2-propynyl melting at 66° C.

NMR Spectrum (deuterochloroform)

Peaks at 2.3–2.4 ppm (hydrogen of hydroxy);
Peaks at 2.51–2.55–2.59 ppm (hydrogen of —C≡CH of propynyl);
Peaks at 2.61–2.65 ppm (hydrogen

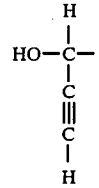

Peaks at 4.77–4.82 ppm (hydrogens of the methylene of —CH$_2$—C≡CH)
Peaks at 5.40 ppm (hydrogen of

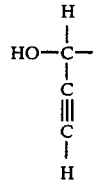

Peaks at 6.90–6.93 ppm and 7.17–7.20 ppm (3- and 5-hydrogens of pyrrole)

STEP B:

[1-(2-Propynyl-2-cyano-1H-pyrrol-4-yl]-propynyl-2-(1R,cisΔE) 2,2-dimethyl-3-(2-fluoro-3-ethoxy-3-oxo-1-propenyl)-cyclopropane carboxylate The following reaction was conducted to obtain the above compound

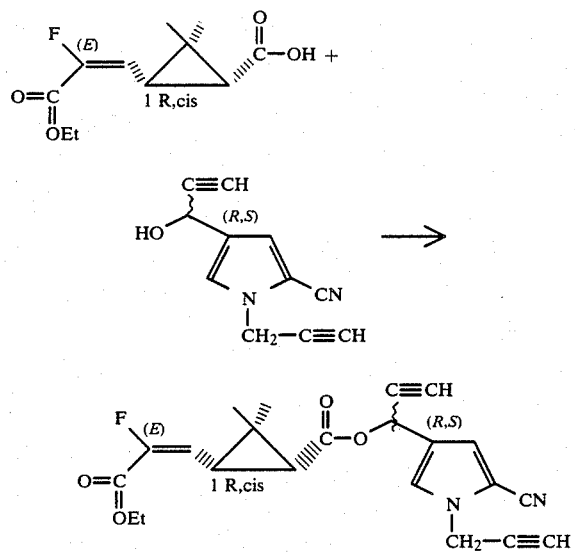

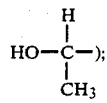

[α]$_D$ = +19°±2° (c=0.5% toluene).

EXAMPLE 58

(R,S)-cyano-[1-(2-propenyl)-2-cyano-1H-pyrrol-4-yl]methyl 1R,cis (E) 2,2-dimethyl-3-[2-fluoro-3-ethoxy-3-oxo-1-propenyl]cyclopropane carboxylate The following reaction was conducted to obtain the above compound

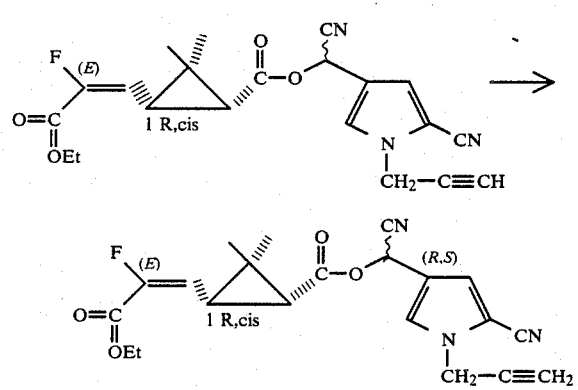

[α]$_D$ = +39.5° (c=0.4% toluene)

EXAMPLE 59

[1-(2-propynyl)-2-cyano-1H-pyrrol-4-yl]-1-ethyl (1R,cis)2,2-dimethyl-3-(2,2-dibromoethenyl)-cyclopropane carboxylate STEP A: 2-cyano-4-[1(R,S) hydroxyethyl-1-(2-propynyl)-1H-pyrrole A solution of 4 g of 1-(2-propynyl)-2-cyano-4-formyl-1H-pyrrole in 45 ml of tetrahydrofuran was slowly introduced at +10° C. into 50 ml of a solution of methyl magnesium iodide in tetrahydrofuran titrating 1.7 mmol/l. After stirring for 4 hours at 20° C., the reaction mixture was poured into a saturated aqueous solution of monosodium phosphate, and extracted with ether. The extracts were concentrated to dryness by distilling under reduced pressure, and the residue was chromatographed on silica. Elution with a mixture of hexane and ethyl acetate (1-1) yielded 2.855 g of 2-cyano-4-[1(R,S) hydroxyethyl-1-(2-propynyl)-1H-pyrrole melting at <50° C.

NMR Spectrum (deuterochloroform)

Peaks at 1.4-1.5 ppm (hydrogens of methyl);

Peaks at 2.50-2.54-2.58 ppm (hydrogen of —C≡C—H);

Peaks at 4.68-4.80 and 4.90-5.03 ppm (hydrogen of

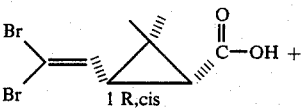

Peaks at 4.76-4.80 ppm (hydrogens of methylene of CH$_2$—C≡C—H)

Peaks at 6.80-6.83 ppm and 4.91 and 5.03 ppm (3- and 5-hydrogens of pyrrole)

STEP B:

[1-(2-propynyl)-2-cyano-1H-pyrrol-4-yl]-1-ethyl (1R,cis) 2,2-dimethyl-3-(2,2-dibromoethenyl)-cyclopropane carboxylate The following reaction was effected to prepare the above compound

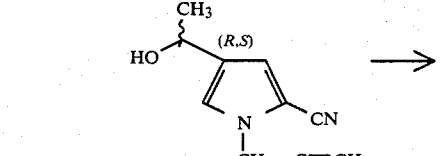

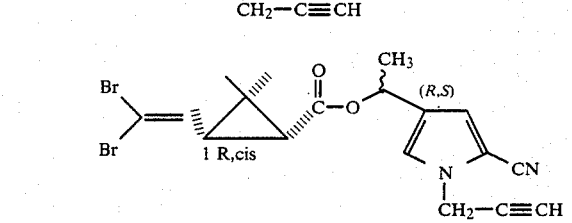

[α]$_D$ = −6.5°±2° (c=6% toluene)

EXAMPLE 60

[1-(2-propynyl)-2-cyano-1H-pyrrol-4-yl]-ethyl (1R,cisΔE) 2,2-dimethyl-3-(2-fluoro-3-ethoxy-3-oxo-1-propenyl)-cyclopropane carboxylate The following reaction was effected to produce the above compound.

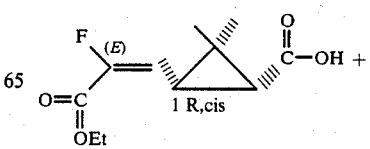

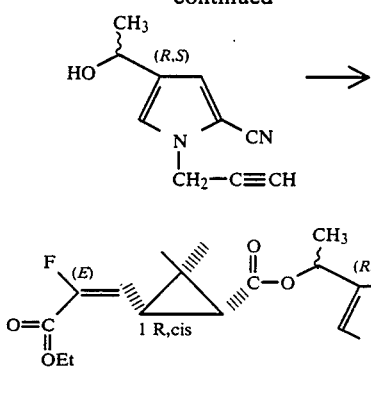

$[\alpha]_D = +21° \pm 2°$ (c=0.6% toluene)

EXAMPLE 61

1R,S-[1-2-propynyl)-2-cyano-1H-pyrrol-4-yl]-propyn-2-yl(1R,cis)
2,2-dimethyl-3-(2,2-dibromoethenyl)-cyclopropane carboxylate The following reaction was effected to produce the above compound.

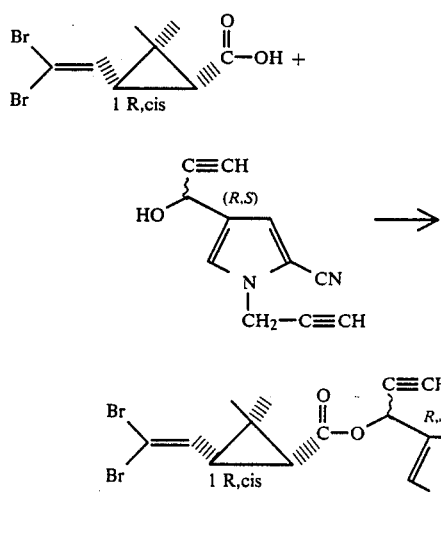

$[\alpha]_D = 10° \pm 2°$ (c=0.5% toluene).

EXAMPLE 62

[1-(2-propynyl)-4-cyano-1H-pyrrol-3-yl]-methyl (1R,cis)
2,2-dimethyl-3-(2,2-dibromoethenyl)-cyclopropane carboxylate The following reaction was effected to produce the above named compound.

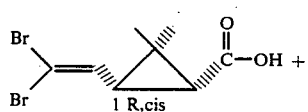

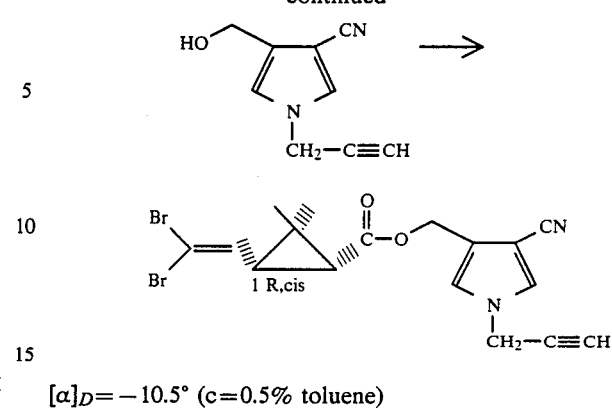

$[\alpha]_D = -10.5°$ (c=0.5% toluene)

EXAMPLE 63

[1-(2-propynyl)-4-cyano-1H-pyrrol-3-yl]-methyl (1R,cis,ΔE)
2,2-dimethyl-3-(2-fluoro-3-ethoxy-3-oxo-1-propenyl-cyclopropane carboxylate The following reaction was conducted to form the above compound.

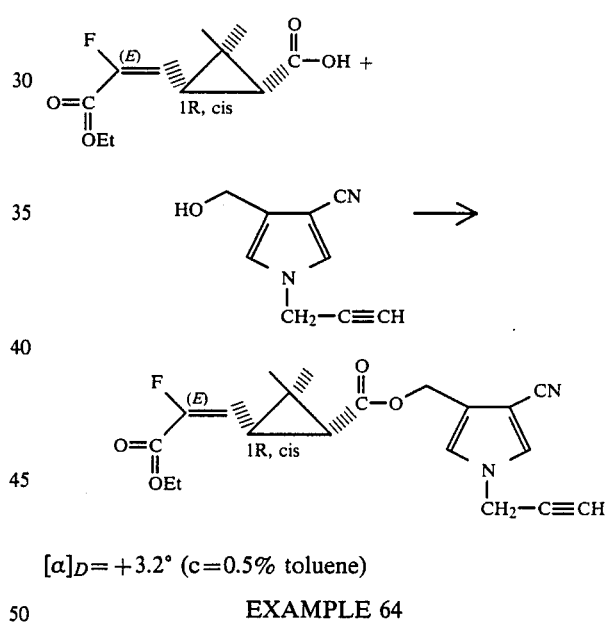

$[\alpha]_D = +3.2°$ (c=0.5% toluene)

EXAMPLE 64

(R,S)-cyano-[1-(2-propynyl)-4-cyano-1H-pyrrol-3-yl]-1-methyl (1R,cis)
2,2-dimethyl-3-(2,2-dibromoethenyl)-cyclopropane carboxylate Step A: methyl 1,3-butadiene (1,4-bis dimethylamino)-2-cyano-3-carboxylate 23 g of methyl α-cyano propionate and 126 ml of tertbutoxy bis(dimethylamino) methane were mixed together and heated at 170° C. for 5 hours. In the beginning, isobutanol distilled off and the reaction mixture was allowed to cool to 50° C. The mixture was subjected to vacuum of 0.1 mm of mercury and heated at 110° C. for 1 hour. (Chromatography over silica and elution with a mixture of hexane and ethyl acetate (1–9) yielded 15.9 g of methyl 1,3-butadiene (1,4-bis dimethylamino)-2-cyano-3-carboxylate melting at 106° C.

STEP B: methyl 3-cyano-1-(2-propynyl)-1H-pyrrole-4-carboxylate 14.5 g of methyl 1,3-butadiene 1,4-bis(dimethylamino)-2-cyano-3-carboxylate, 400 ml of ethanol and 4.2 ml of monopropargylamine were mixed together and refluxed for 5 hours. The reaction mixture was then cooled and poured into a saturated aqueous solution of sodium chloride and extracted with methylene chloride. The extracts were concentrated to dryness by distilling under reduced pressure and the residue was chromatographed over silica. Elution with a mixture of hexane and ethyl acetate (65–35) yielded. 3.75 g of methyl 3-cyano-1-(2-propynyl)-1H-pyrrole-4-carboxylate melting at 134° C.

STEP C: 4-hydroxymethyl-1-(2-propynyl)-1H-pyrrole-3-carbonitrile 3.90 g of methyl 3-cyano-1-(2-propynyl)-1H-pyrrole-4-carboxylate, 35 ml of tetrahydrofuran, 11 ml of water and 1.556 g of lithium borohydride were mixed together and stirred for 3 hours 30 minutes at 20° C. The reaction mixture was poured into a saturated aqueous solution of sodium chloride with stirring and was extracted with ethyl acetate. The extracts were concentrated to dryness by distilling under reduced pressure and the residue was chromatographed over silica. Elution with a mixture of hexane and ethyl acetate (4–6) yielded 1.33 g of 4-hydroxymethyl-1-(2-propynyl)-1H-pyrrole-3-carbonitrile melting at 95° C.

STEP D: 4-formyl-1-(2-propynyl)-1H-pyrrol-3-carbonitrile 18 ml of a molar solution of dimethylsulfoxide in methylene chloride were introduced dropwise at −60° C. into 9.5 ml of a molar solution of oxalyl chloride in methylene chloride and the mixture was stirred at −60° C. for 5 minutes. Then, at −60° C., a solution of 724 g of 4-hydroxyl-methyl-1-(2-propynyl)-1H-pyrrole-3-carbonitrile was added dropwise and the mixture was stirred at −60° C. for 5 hours, after which, still at −60° C., 25 ml of a molar solution of triethylamine in methylene chloride were added dropwise. The mixture was stirred at −60° C. for 30 minutes and the reaction mixture was allowed to return to ambient temperature. Water was added and the mixture was stirred and decanted. The organic phase was washed with a saturated aqueous solution of sodium chloride and concentrated to dryness by distilling under reduced pressure. The residue was chromatographed over silica and was eluted with a mixture of hexane and ethyl acetate (1–1) to obtain 702 mg of 4-formyl-1-(2-propynyl)-1H-pyrrol-3-carbonitrile melting at 114° C.

STEP E: 4-[(R,S) α-cyano-methanol]-1-(2-propynyl)-1H-pyrrole-3-carbonitrile 495 mg of 4-formyl-1-(2-propynyl)-1H-pyrrole-3-carbonitrile, 15 ml of methanol, 2.1 ml of water, 1.2 ml of acetic acid and 900 mg of sodium cyanide were mixed together and after allowing the temperature to return to 20° C., the mixture was stirred for 15 minutes at 20° C. The mixture was washed with water, extracted with ethyl acetate and concentrated to dryness by distillation under reduced pressure to obtain a crude product which was used as is for the next step.

STEP F: (R,S) cyano-[1-(2-propynyl)-4-cyano-1H-pyrrol-3-yl]-1-methyl (1R,cis) 2,2-dimethyl-3-(2,2-dibromoethenyl)-cyclopropane carboxylate The following reaction was effected to produce the above compound.

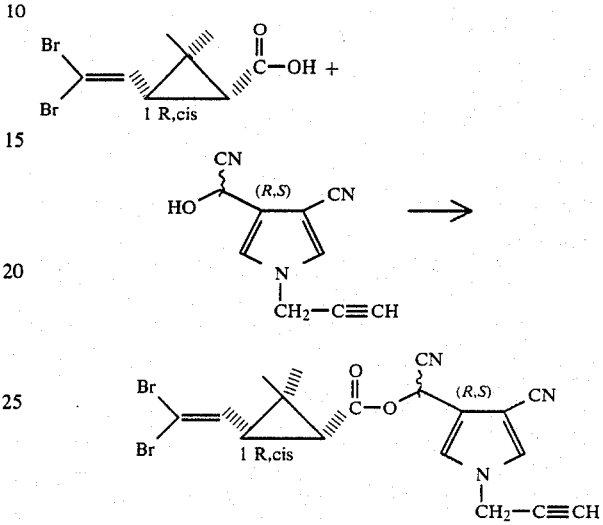

$[\alpha]_D = -15.5°$ (c=0.5% toluene).

EXAMPLE 65

[2-cyano-[1-(3-chloro-2-(Z)-propenyl]-1H-pyrrol-4-yl]-methyl (1R,cis,ΔE) 2,2-dimethyl-3-(2-fluoro-3-ethoxy-3-oxo-1-propenyl)-cyclopropane carboxylate

STEP A: (cis,trans) 4-formyl-2-cyano-1-(3-chloro-2-propenyl)-1H-pyrrole 4.15 g of 2-cyano-4-formyl-1H-pyrrole were introduced into 20 ml of dimethylformamide, and after cooling to +10° C., 1.563 g of sodium hydride as 55% dispersion in oil were added in small quantities, followed by stirring for 30 minutes at +15° C. After cooling to +5° C., 32 ml of 1,3-dichloropropane were introduced over 20 minutes followed by stirring for 2 hours at +15° C. The reaction mixture was poured into water and was extracted with ether. By drying, concentration the ethereal phases, chromatographing the residue over silica and eluting with a mixture of hexane and ethyl acetate (1–1), 6.4 g of (cis,trans) 4-formyl-2-cyano-1-(3-chloro-2-propenyl)-1H-pyrrole were obtained.

STEP B: (cis,trans) 4-hydroxymethyl-2-cyano-1-(3-chloro-2-propenyl)-1H-pyrrole 4 g of the product of Step A, 100 ml of tetrahydrofuran, 22 ml of distilled water and 4.4 g of potassium borohydride were stirred for 45 minutes and then ethyl ether was added. The mixture was stirred for 2 hours and the organic phase was decanted. The aqueous phase was extracted again with ether and the combined organic phases were dried and evaporated to dryness to obtain (cis,trans) 4-hydroxymethyl-2-cyano-1-(3-chloro-b 2-propenyl)-1H-pyrrole.

STEP C:
[2-cyano-1-[3-chloro-2-(Z)-propenyl]-1H-pyrrole-4-yl]-
methyl (1R,cis,ΔE)
2,2-dimethyl-3-[2-fluoro-3-ethoxy-3-oxo-1-propenyl]-
cyclopropane carboxylate 1.55 g of [2-cyano-1-[3-chloro-2-(Z+E)-propenyl]-1H-pyrrol-4-yl]-methanol, 1.8 g of (1R, cisΔE) 2,2-dimethyl-3-(2-fluoro-3-ethoxy-3-oxo-1-propenyl)-cyclopropane carboxylic acid and 20 ml of dichloromethane were mixed together and then, at +5° C., a mixture of 1.625 g of dicyclohexylcarbodiimide, 10 ml of dichloromethane and 29 mg of 4-dimethylaminopyridine were introduced progressively. The mixture was stirred for 20 hours at 20° C. and after filtering, the filtrate was concentrated to dryness by distilling under reduced pressure. The residues was chromatographed over silica and eluted with a mixture of hexane and ethyl acetate (7-3), then with a mixture of hexane and ethyl acetate (9-1) to obtain 0.83 g of [2-cyano-1-[3-chloro-2-(Z)-propenyl]-1H-pyrrole-4-yl]-methyl (1R,cis,ΔE) 2,2-dimethyl-3-[2-fluoro-3-ethoxy-3-oxo-1-propenyl]-cyclopropane carboxylate with a specific rotation of $[\alpha]_D = +32.5°$ (c=0.8% toluene)

EXAMPLE 66
[2-cyano-1-[3-chloro-2-(E)-propenyl]-1H-pyrrol-4-yl]-
methyl (1R,cisΔE)
2,2-dimethyl-3-[2-fluoro-3-ethoxy-3-oxo-1-propenyl]-
cyclopropane carboxylate By continuing the chromatography of Example 65, 0.32 g of the above product were obtained with a specific roation of $[\alpha]_D = +28°$ (c=0.5% toluene)

EXAMPLE 67
(R,S)
cyano[1-(2-propynyl)-2-cyano-1H-pyrrol-3-yl]-methyl
(1R,cisΔE)
2,2-dimethyl-3-(2-fluoro-3-ethoxy-3-oxo-1-propenyl)-
cyclopropane carboxylate STEP A: 3-formyl-2-cyano-1-(2-propynyl)-1H-pyrrole 27 ml of a 1M solution of oxalyl chloride in methylene chloride were cooled to −60° C. and 13.5 ml of a 1M solution of dimethyl sulfoxide in methylene chloride were added. After stirring for 5 minutes, a solution of 1.09 g of 3-hydroxymethyl-1-(2-propynyl)-1H-pyrrole-2-carbonitrile in 20 ml of methylene chloride was added, and the temperature was kept at −60° C. for 2 hours. 70 ml of a 1M solution of triethylamine in methylene chloride were added with stirring for 10 minutes at −60° C., and the temperature was allowed to rise to 20° C. 20 ml of water were added, followed by stirring, decanting and concentrating to dryness. The residue was chromatographed over silica and eluted with a mixture of hexane and ethyl acetate (6-4) to obtain 456 mg of 3-formyl-2-cyano-1-(2-propynyl)-1H-pyrrole.

NMR Spectrum (CDCl₃)
Peaks at 2.59–2.63–2.65 ppm (proton of —C≡CH);
Peaks at 6.75–6.8 and 7.15–7.18 ppm (protons of pyrrole);
Peaks at 4.9–4.95 ppm (protons of CH₂ of propynyl);
Peaks at 10 ppm (proton of formyl).

STEP B: 2-hydroxy-(R,S)
2-cyano-1-(2-propynyl)-1H-pyrrole-3-acetonitrile

Using the procedure of Step E of Example 65, 546 mg of 3-formyl-2-cyano-1-(2-propynyl)-1H-pyrrole were reacted to obtain 2-hydroxy-(R,S) 2-cyano-1-(2-propynyl)-1H-pyrrole-3-acetonitrile.

STEP C: (R,S)
cyano-[1-(2-propynyl)-2-cyano-1H-pyrrol-3-yl]-methyl
(1R,cisΔE)
2,2-dimethyl-3-(2-fluoro-3-ethoxy-3-oxo-1-propenyl)-
cyclopropane carboxylate The following reaction was effected to produce the above compound.

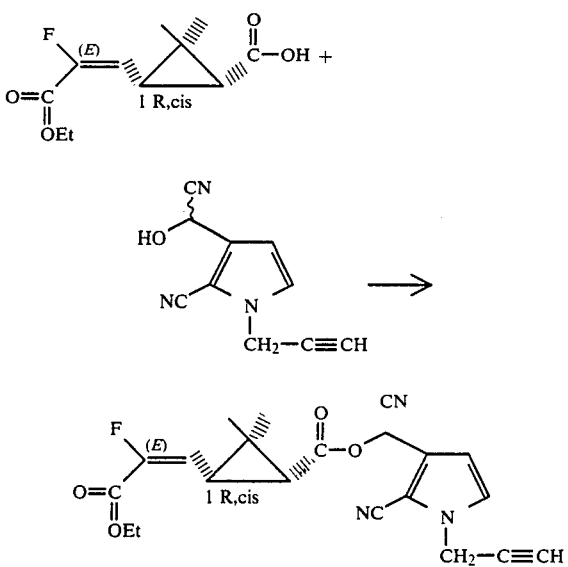

$[\alpha]_D = +21°$ (c=0.5% toluene).

EXAMPLE 68
(R,S)
cyano-[1-(2-propynyl)-3-cyano-1H-pyrrol-4-yl]-methyl
(1R,cisΔE)
2,2-dimethyl-3-[2-fluoro-3-ethoxy-3-oxo-1-propenyl]-
cyclopropane carboxylate Using the procedure of Example 1, the following reaction was effected to obtain the above compound.

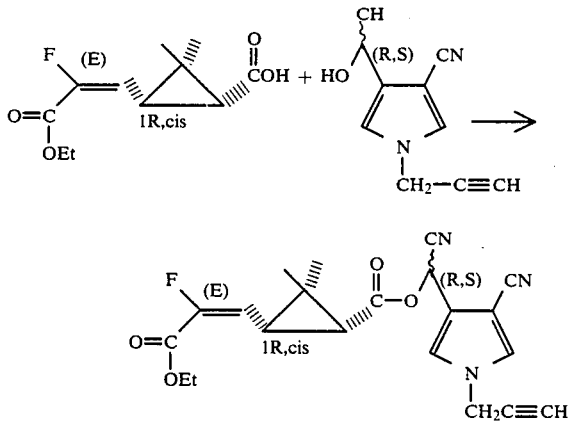

$[\alpha]_D = +12.5°$ (c=0.6% toluene)

EXAMPLE 69

(R,S) cyano-[1-(2-propynyl)2,2,2-trifluoromethyl-1H-pyrrol-4-yl]-methyl (1R,cis,ΔZ) 2,2-dimethyl-3-[3-methoxy-3-oxo-1-propenyl]-cyclopropane carboxylate

STEP A: ethyl 4-[1-(2-propynyl)-2-trifluoromethyl-1H-pyrrole]-carboxylate 9 g of 3-aza-5-hexyn-1-oic acid hydrochloride, 120 ml of toluene and 9.15 ml of ethyl propionate were mixed together and then, at +5° C., 18.6 ml of trifluoroacetic anhydride were introduced progressively. The reaction mixture was refluxed for 4¾ hours and then was cooled to +30° C. 9.3 ml of trifluoroacetic anhydride were added, and the reaction mixture was refluxed for 5 hours and stirred for 10 hours at 20° C. 5.6 ml of acetic anhydride were added, and the reaction mixture was refluxed for 2 hours. After cooling, the reaction mixture was poured into water and ether was added, followed by neutralization with a saturated solution of sodium bicarbonate. By extracting with ether, concentrating to dryness by distilling under reduced pressure, chromatographing the residue over silica and eluting with a mixture of hexane and ethyl acetate (8-2), 3.964 g of ethyl 4-[1-(2-propynyl)-2-trifluoromethyl-1H-pyrrole]-carboxylate were obtained melting at <50° C.

IR Spectrum (chloroform)
absorption at 1712 cm$^{-1}$ (ester

)

absorption at 3140 cm$^{-1}$, 1572 cm$^{-1}$, 1519 cm$^{-1}$, (heterocycle =CH)
absorption at 1187 cm$^{-1}$, 1162 cm$^{-1}$, 1116 cm$^{-1}$ (CF$_3$)
absorption at 3307 cm$^{-1}$ (C≡CH, ≡CH)
absorption at 2125 cm$^{-1}$ (C≡C)

STEP B: 2-trifluoromethyl-1-(2-propynyl)-1H-pyrrole-4-methanol 4.785 g of ethyl 4-[1-(2-propynyl)-2-trfluoromethyl-1H-pyrrol]-carboxylate were dissolved in 40 ml of tetrahydrofuran and at 0° C., 750 mg of lithium-aluminium hydride were added in small portions. The mixture was stirred for 30 minutes at +7° C. then 3 hours at 20° C., after which a few drops of ethyl acetate and 10 ml of a saturated aqueous solution of disodium tartrate were added. The reaction mixture was filtered and the filtrate was concentrated to dryness by distilling under reduced pressure. The residue was chromatographed over silica and eluted with a mixture of hexane and ethyl acetate (6-4) to obtain 3.45 g of 2-trifluoromethyl-1-(2-propynyl)-1H-pyrrole-4-mehanol.

IR Spectrum (chloroform)
absorption at 3610 cm$^{-1}$ (—OH)
absorption at 3308 cm$^{-1}$ (—C≡CH)
absorption at 1580 cm$^{-1}$, 1510 cm$^{-1}$,

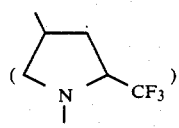

STEP C: (R,S) cyano-[1-(2-propynyl)-2-trifluoromethyl-1H-pyrrol-4-yl]-methyl (1R,cisΔZ) 2,2-dimethyl-3-[3-(3-methoxy-3-oxo-1-propenyl]-cyclopropane carboxylate The following reaction was effected to obtain the above compound.

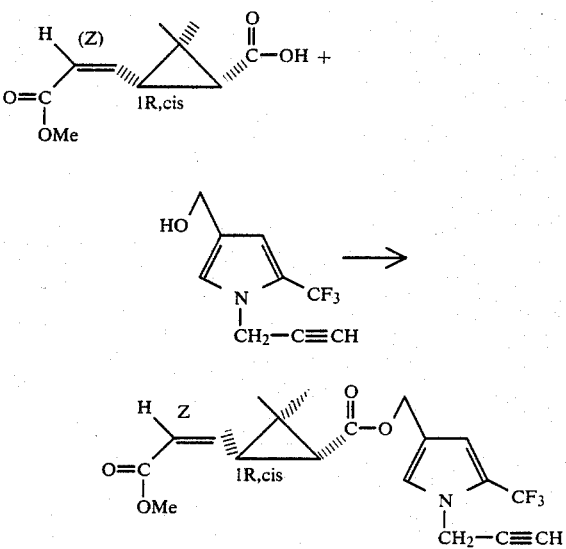

$[\alpha]_D = +59° \pm 4°$ (c=0.4% toluene)

EXAMPLE 70

[1-(2-propynyl)-2,2,2-trifluoromethyl-1H-pyrrol-4-yl]-methyl (1R,cis,ΔE) 2,2-dimethyl-3-[2-fluoro-3-ethoxy-3-oxo-1-propenyl]-cyclopropane carboxylate The following reaction was effected to obtain the above compound.

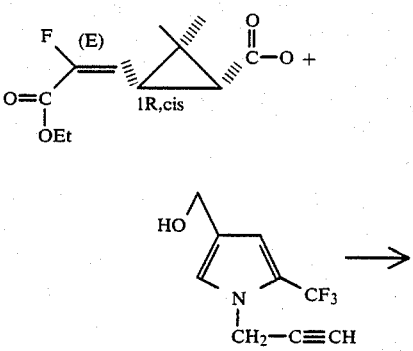

-continued

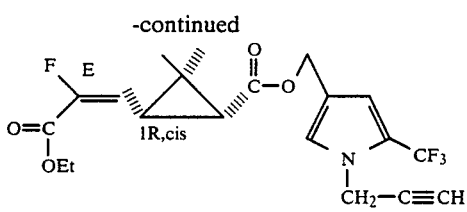

$[\alpha]_D = +40.5° \pm 2.5°$ (c=0.5% toluene)

EXAMPLE 71

[1-(2-propynyl)-3,3,3-trifluoromethyl-1H-pyrrol-4-yl]-methyl (1R,cis,ΔZ) 2,2-dimethyl-3-[3-methoxy-3-oxo-1-propenyl]-cyclopropane carboxylate The following reaction was effected to obtain the above compound,

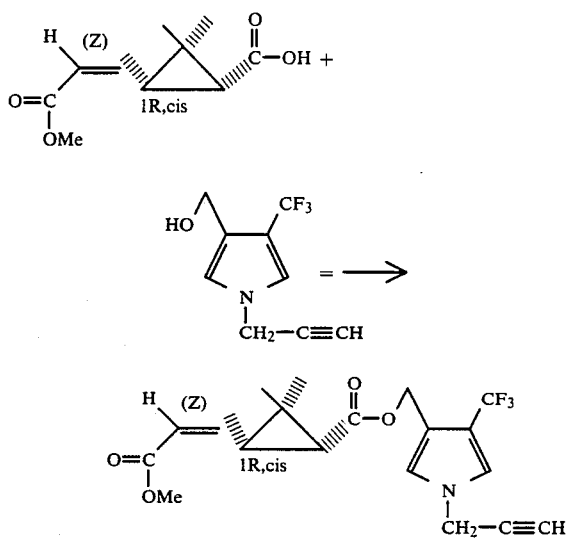

$[\alpha]_D = +41.5°$ (c=0.5% chloroform)

EXAMPLE 72

[1-(2-propynyl)-3,3,3-trifluoromethyl-1H-pyrrol-4-yl]methyl (1R,cis,ΔE) 2,2-dimethyl-3-[2-fluoro-3-ethoxy-3-oxo-1-propenyl]-cyclopropane carboxylate The following reaction was effected by the procedure of Example 1 to obtain the above compound.

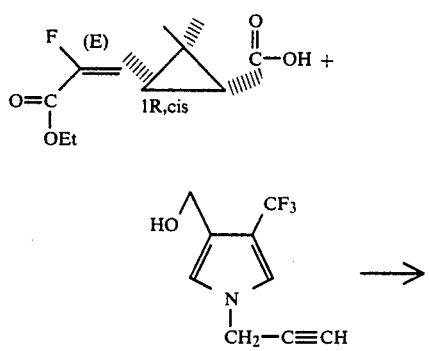

-continued

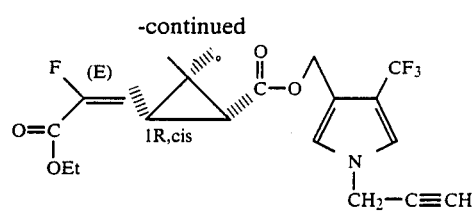

$[\alpha]_D = +23.5° \pm 3°$ (c=0.2% chloroform)

EXAMPLE 73

[2-cyano-1-[3-chloro-2-(Z)-propenyl]-1H-pyrrol-4-yl]-methyl (1R,cis) 2,2-dimethyl-3-(2,2-dibromoethenyl)-cyclopropane carboxylate Using the procedure of Example 65, the following reaction was effected to obtain the above compound.

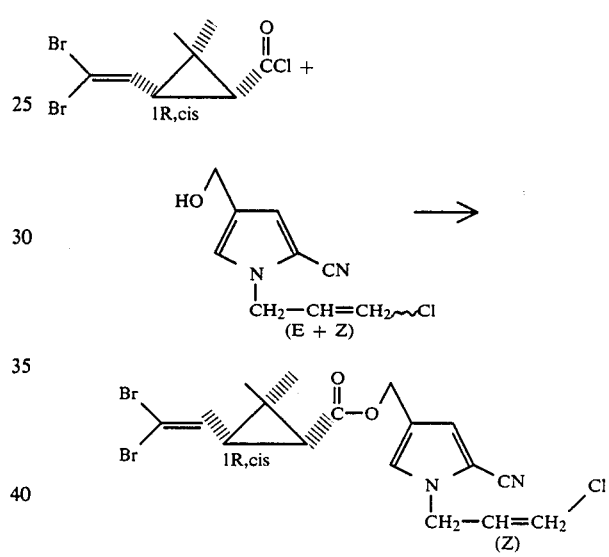

$[\alpha]_D = -6°$ (c=1% toluene)

EXAMPLE 74

[2-cyano-1-[3-chloro-2-(E)-propenyl]-1H-pyrrol-4-yl]-methyl (1R,cis) 2,2-dimethyl-3-(2,2-dibromoethenyl)-cyclopropane carboxylate Using the procedure of Examle 65, the following reaction was effected to obtain the above compound.

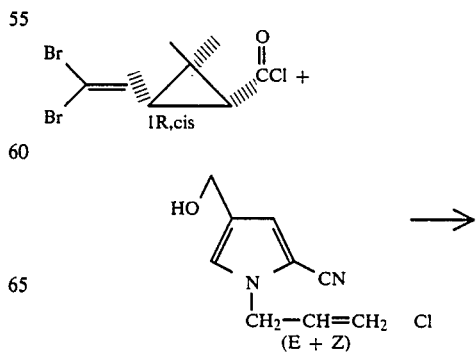

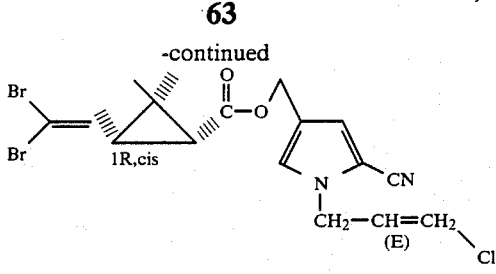

$D = -4°$ (c=0.6% toluene).

EXAMPLE 75

Preparation of a soluble concentrate

A homogeneous mixture was prepared of 0.25 g of Product of Example 1, 1.00 g of Piperonyl butoxide, 0.25 g of Tween 80, 0.1 g of Topanol A and 98.4 g of water.

EXAMPLE 76

Preparation of an emulsifiable concentrate

There were mixed intimately 0.015 g of the Product of Example 2, 0.5 g of Piperonyl butoxide, 0.1 g of Topanol A, 3.5 g of Tween 80 and 95.885 g of xylene.

EXAMPLE 77

Preparation of an emulsifiable concentrate

A homogeneous mixture was prepared of 1.5 g of the Product of Example 40, 20.00 g of Tween 80, 0.1 g of Topanol A and 78.4 g of xylene.

EXAMPLE 78

There was mixed homogeneously 0.25 g of the Product of Example 1, 25.00 g of Tabu powder, 40.00 g of Cedar leaf powder, 33.75 g of Pine wood powder, 0.5 g of Brilliant green and 0.5 g of p-nitrophenol.

EXAMPLE 79

Example of a food compound for animals

As a balanced basic foodstuff, a foodstuff was used which comprised of corn, dehydrated lucerne, wheat straw, cabbage-palm cake with molasses, urea and a vitaminized mineral condiment. This foodstuff contains a minimum of 11% of crude protein substances (2.8% from the urea), 2.5% of fatty substances, a maximum of 15% of cellulose substances, 6% of minerals and 13% humidity. The foodstuff used corresponded to 82 fodder units per 100 kilograms and per 100 kilograms contained 910,000 I.U. of A vitamins, 91,000 I.U. of vitamin $D_3$, 150 mg of vitamine E, 150 mg of vitamin C. In this foodstuff, 0.3 kg of the compound of Example 1 were incorporated per 100 kg of total foodstuff.

EXAMPLE 80

Example of compound aliment for animals

The same balanced basic foodstuff was used as in Example 79 and there was incorporated 0.04 kg of the compound of Example 1 for 100 kg of total foodstuff.

BIOLOGICAL STUDY (1) Study of knock-down activity of house flies

The test insects were female house flies 4 days old and the test was effected by direct atomization in a Kearns and March chamber using as solvent a mixture of acetone (5%) and Isopar L (petrol solvent) (quantity of solvent used, 2 ml in one second). 50 insects were used per treatment and checks were made every minute for 10 minutes, then at 15 minutes, and the $KT_{50}$ was determined by the usual methods. The following results were obtained:

| Compound of example | KT 50 (in min) concentration at 0.1 g/l | Compound of example | KT 50 (in min) concentration at 0.1 g/l |
| --- | --- | --- | --- |
| 1 | 1.3 | 50 | 3.5 |
| 2 | 1.6 | 56 | 4.0 |
| 3 | 5.8 | 43 | 2.9 |
| 4 | 2.4 | 53 | 2.4 |
| 5 | 3.2 | 54 | 4.7 |
| 6 | 4.7 | 55 | 8.7 |
| 15 | 1.8 | 60 | 1.8 |
| 26 | 3.5 | 57 | 4.0 |
| 40 | 5.6 | 65 | 3.1 |
| 44 | 2.2 | 66 | 7.9 |
| 48 | 3.7 | 67 | 3.8 |
| 51 | 1.9 | 45 | 6.1 |
| 52 | 1.5 | 72 | 3.8 |
| 49 | 11.0 | 69 | 4.8 |
|  |  | 70 | 3.9 |

Conclusion: The products were endowed with a very good knock-down effect on house flies.

(2) Study of activity by tarsal contact on cockroaches

The insects tested were male cockroaches (Blatella germanica) and the test was carried out by depositing an acetone solution of a certain concentration on the bottom of a Petri dish 20 cm in diameter. After this had dried, 20 male cockroaches were allowed to stay there per concentration for 1 hour, after which they were transferred to a healthy medium and their mortality was checked at 24 hours, 48 hours, 3 days and 5 days. The result was expressed as lethal concentration 50 (LC 50) in mg/m².

| Example | LC 50 |
| --- | --- |
| 43 | 2.8 |
| 45 | 6.4 |
| 72 | 6.7 |
| 70 | 4.5 |

Conclusion: The products were endowed with an insecticide activity on cockroaches.

(3) Study of lethal effect on Aphis cracivora

Adults 7 days old were used with 10 aphis per concentration using a contact-ingestion method. The treatment was carried out with a Fisher gun on a bean leaf which was placed in a plastic Petri dish on a disc of moistened paper. 2 ml of an acetone solution of the product under test were used with 1 ml per face of the leaf and the insect infestation was carried out after drying the leaf. The insects were kept in contact with the leaf for 1 hour and then they were placed on untreated leaves. Mortality was checked after 24 hours and the experimental results obtained are summarized in the following table:

| Example | LD 50 in mg/insect |
| --- | --- |
| 49 | 6.5 |
| 43 | 7.5 |

Conclusion: The products were endowed with a lethal effect on Aphis cracivora (4) Activity on *Tetranychus urticae*, test of lethal effect on adults Bean plants having two cotyledon leaves were used which were treated with a Fisher gun with an acetone solution of the product. After drying, 25 females of the acaridan *Tetranychus urticae* were placed on each leaf, that is 50 individuals per experimental dose per plant. The efficacity was checked after 80 hours of contact, and the LD 50 was indicated in mg/hl.

| Example | LD 50 |
|---------|-------|
| 40 | 32 |
| 43 | 342 |
| 45 | 264 |
| 70 | 2126 |

Conclusion: The products and particularly that of Example 40 were endowed with a remarkable acaricidal effect on *Tetranychus urticae*.

Various modifications of the products and process of the invention may be made without departing from the spirit or scope thereof and it is to be understood that the invention is intended to be limited only as defined in the appended claims.

What we claim is:

1. A pyrrole derivatives of the formula

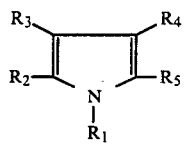
I wherein one of $R_2$ and $R_3$ is

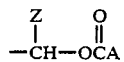

and the other of $R_2$ and $R_3$ as well as $R_4$ and $R_5$ are individually selected from the group consisting of hydrogen, halogen, alkyl of 1 to 18 carbon atoms, aryl of 6 to 14 carbon atoms, aralkyl of 7 to 18 carbon atoms, —CN, —CF$_3$, —NO$_2$, Z is selected from the group consisting of hydrogen, —CN, —C≡CH, —CF$_3$ and alkyl of 1 to 3 carbon atoms, A is

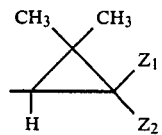

and $Z_1$ and $Z_2$ are both methyl or $Z_1$ is hydrogen and $Z_2$ is selected from the group consisting of

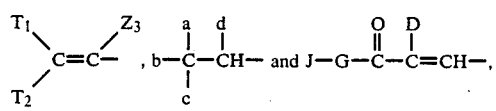

$Z_3$ is hydrogen or halogen, $T_1$ and $T_2$ are individually selected from the group consisting of hydrogen, halogen, —CF$_3$, —CN, alkyl and alkoxy of 1 to 8 carbon atoms, and phenyl optionally substituted by a halogen and taken together with the carbon they are attached to form a cycloalkyl of 3 to 6 carbon atoms a, b, c and d are individually halogen, D is selected from the group consisting of hydrogen, halogen and alkoxy of 1 to 8 carbon atoms, G is oxygen or sulfur, J is selected from the group consisting of alkyl of 1 to 8 carbon atoms optionally substituted with at least one member of the group consisting of halogen, hydroxy, alkoxy of 1 to 8 carbon atoms, —NH$_2$ and mono- and dialkylamino of 1 to 8 alkyl carbon atoms, cycloalkyl of 3 to 8 carbon atoms phenyl or A may be

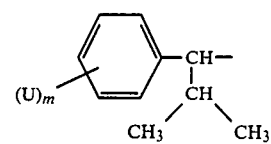

U may be halogen or alkyl or alkoxy of 1 to 8 carbon atoms and m is 0, 1 or 2 $R_1$ is selected from the group consisting of

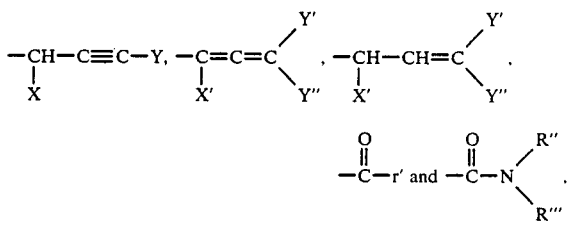

X', X, Y, Y' and Y" are individually selected from the group consisting of hydrogen, halogen, alkyl of 1 to 8 carbon atoms and phenyl, r' is selected from the group consisting of hydrogen, alkyl of 1 to 18 carbon atoms, phenyl, phenylalkyl of 7 to 18 carbon atoms, CF$_3$—, —COOAlk and alkoxy of 1 to 8 carbon atoms and Alk is alkyl of 1 to 8 carbon atoms, R" and R"' are individually selected from the group consisting of hydrogen, alkyl of 1 to 18 carbon atoms, phenyl, phenylalkyl of 7 to 18 carbon atoms, —CF$_3$, —COOAlk' and alkoxy of 1 to 8 carbon atoms and Alk' is alkyl of 1 to 8 carbon atoms.

2. A compound of claim 1 wherein $R_1$ is —CH$_2$—C≡CH.

3. A compound of claim 1 wherein Z is

is hydrogen.

4. A compound of claim 1 wherein Z is cyano in

5. A compound of claim 1 wherein $R_3$ is

6. A compound of claim 1 wherein $R_2$, $R_4$ and $R_5$ are hydrogen.

7. A compound of claim 1 wherein one of $R_2$, $R_4$ and $R_5$ is —NO$_2$.

8. A compound of claim 1 wherein one of $R_1$, $R_4$ and $R_5$ is cyano.

9. A compound of claim 1 wherein one of $R_2$, $R_4$ and $R_5$ is —$CF_3$.

10. A compound of claim 1 wherein A may be

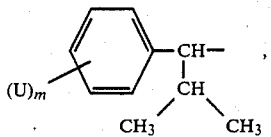

U may be halogen or alkyl or alkoxy of 1 to 8 carbon atoms and m is 0, 1 or 2.

11. A compound of claim 1 wherein A is

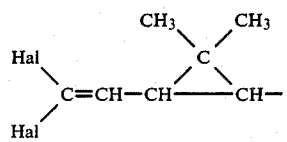

and Hal is halogen.

12. A compound of claim 1 wherein A is

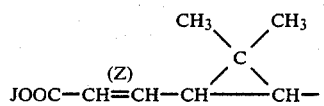

and J is alkyl of 1 to 8 carbon atoms or cycloalkyl of 3 to 8 carbon atoms and the double bond has geometry z.

13. A compound of claim 1 wherein A is

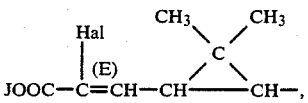

Hal is halogen, J is alkyl of 1 to 8 carbon atoms and the double bond has geometry E.

14. A compound of claim 1 wherein Hal is fluorine.

15. A compound of claim 1 selected from the group consisting of [1-(2-propynyl)-1H-pyrrol-3-yl]-methyl (1R,cisΔE) 2,2-dimethyl-3-(3-ethoxy-3-oxo-2-fluoro-1-propenyl)-cyclopropane carboxylate; [1-(2-propynyl)-1H-pyrrol-3-yl]-methyl (1R,cis,ΔZ) 2,2-dimethyl-3-(3-methoxy-3-oxo-1-propenyl)-cyclopropane carboxylate; and [1-(2-propynyl)-2-trifluoromethyl-1H-pyrrol-3-yl]-methyl (1R,cis,ΔE) 2,2-dimethyl-3-(3-ethoxy-3-oxo-2-fluoro-1-propenyl)-cyclopropane carboxylate.

16. A compound of claim 1 which is [1-(2-propynyl)-2-trifluoromethyl-(1H-pyrrol-3-yl)]-methyl (1R,cis,ΔE) 2,2-dimethyl-3-(3-tert-butoxy-3-oxo-2-fluoro-1-propenyl)-cyclopropane carboxylate.

17. A pesticidal composition comprising a pesticidally effective amount of at least one compound of claim 1 and an inert carrier.

18. A composition of claim 17 wherein $R_1$ is —$CH_2$—≡$CH$.

19. A composition of claim 17 wherein Z in

is hydrogen.

20. A composition of claim 17 wherein Z is cyano in

21. A composition of claim 17 wherein $R_3$ is

22. A composition of claim 17 wherein $R_2$, $R_4$ and $R_5$ are hydrogen.

23. A composition of claim 17 wherein one of $R_2$, $R_4$ and $R_5$ is —$NO_2$.

24. A composition of claim 17 wherein A may be

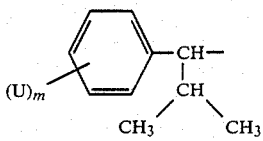

U may be halogen or alkyl or alkoxy of 1 to 8 carbon atoms and m is 0, 1 or 2.

25. A composition of claim 17 wherein A is

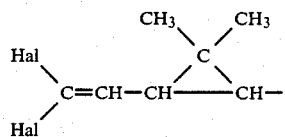

and Hal is halogen.

26. A composition of claim 17 wherein A is

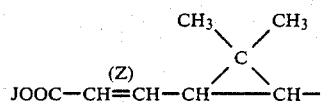

and J is alky- of 1 to 8 carbon atoms or cycloalkyl of 3 to 8 carbon atoms and the double bond has geometry Z.

27. A composition of claim 17 wherein A is

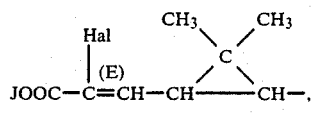

Hal is halogen, J is alkyl of 1 to 8 carbon atoms and the double bond has geometry E.

28. A composition of claim 17 wherein Hal is fluorine.

29. A composition of claim 17 selected from the group consisting of [1-(2-propynyl)-1H-pyrrol-3-yl]-methyl (1R,cis,ΔE) 2,2-dimethyl-3-(3-ethoxy-3-oxo-2-fluoro-1-propenyl)-cyclopropane carboxylate; [1-(2-propynyl)-1H-pyrrol-3-yl]-methyl (1R,cis,ΔZ) 2,2-dimethyl-3-(3-methoxy-3-oxo-1-propenyl)-cyclopropane carboxylate; and [1-(2-propynyl)-2-trifluoromethyl-1H-pyrrol-3-yl]-methyl (1R,cisΔE) 2,2-dimethyl-3-

(3-ethoxy-3-oxo-2-fluoro-1-propenyl)-cyclopropane carboxylate.

30. A composition of claim 17 which is [1-(2-propynyl)-2-trifluoromethyl-(1H-pyrrol-3-yl)]-methyl (1R,cisΔE) 2,2-dimethyl-3-(3-tert-butoxy-3-oxo-2-fluoro-1-propenyl)-cyclopropane carboxylate.

31. A nematocidal composition comprising a nematocidally effective amount of at least one compound of claim 1 and an inert carrier.

32. An acaricidal composition comprising an acaricidally effective amount of at least one compound of claim 1 and an inert carrier.

33. A composition for combatting parasites of warm-blooded animals comprising at least one compound of claim 1 and an inert carrier.

34. A method of combatting insects comprising contacting insects with an insecticidally effective amount of at least one compound of claim 1.

35. A method of claim 34 wherein $R_1$ is $-CH_2-C\equiv CH$.

36. A method of claim 34 wherein Z is

is hydrogen.

37. A method of claim 34 wherein Z is cyano in

38. A method of claim 34 wherein $R_3$ is

39. A method of claim 34 wherein $R_2$, $R_4$ and $R_5$ are hydrogen.

40. A method of claim 34 wherein one of $R_2$, $R_4$ and $R_5$ is $-NO_2$.

41. A method of claim 34 wherein one of $R_2$, $R_4$ and $R_5$ is cyano.

42. A method of claim 34 wherein one of $R_2$, $R_4$ and $R_5$ is $-CF_3$.

43. A method of claim 34 wherein A may be

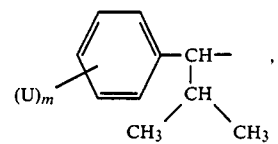

U may be halogen or alkyl or alkoxy of 1 to 8 carbon atoms and m is 0, 1 or 2.

44. A method of claim 34 wherein A is

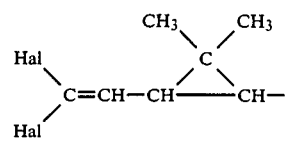

and Hal is halogen.

45. A method of claim 34 wherein A is

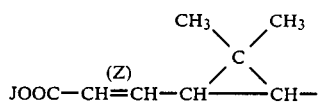

and J is alky- of 1 to 8 carbon atoms or cycloalkyl of 3 to 8 carbon atoms and the double bond has geometry Z.

46. A method of claim 34 wherein A is

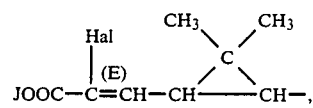

Hal is halogen, J is alkyl of 1 to 8 carbon atoms and the double bond has geometry E.

47. A method of claim 34 wherein Hal is fluorine.

48. A method of claim 34 selected from the group consisting of [1-(2-propynyl)-1H-pyrrol-3-yl]-methyl (1R,cisΔE) 2,2-dimethyl-3-(3-ethoxy-3-oxo-2-fluoro-1-propenyl)-cyclopropane carboxylate; [1-(2-propynyl)-1H-pyrrol-3-yl]-methyl (1R,cisΔZ) 2,2-dimethyl-3-(3-methoxy-3-oxo-1-propenyl)-cyclopropane carboxylate; and [1-(2-propynyl)-2-trifluoromethyl-1H-pyrrol-3-yl]-methyl (1R,cis,ΔE) 2,2-dimethyl-3-(3-ethoxy-3-oxo-2-fluoro-1-propenyl)-cyclopropane carboxylate.

49. A method of claim 34 using is [1-(2-propynyl)]-2-trifluoromethyl-[1H-pyrrol-3-yl]-methyl (1R,cisΔE) 2,2-dimethyl-3-(3-tert-butoxy-3-oxo-2-fluoro-1-propenyl)-cyclopropane carboxylate.

50. A method of combatting nematodes comprising contacting nematodes with a nematocidally effective amount of at least one compound of claim 1.

51. A method of combatting acariens comprising contacting acariens with an acaricidally effective amount of at least one compound of claim 1.

* * * * *

UNITED STATES PATENT AND TRADEMARK OFFICE
CERTIFICATE OF CORRECTION

PATENT NO. : 4,737,513

DATED : April 12, 1988

INVENTOR(S) : JEAN TESSIER, JEAN-PIERRE DEMOUTE and LAURENT TALIANI

It is certified that error appears in the above-identified patent and that said Letters Patent is hereby corrected as shown below:

| Col. | Line | | |
|---|---|---|---|
| 3 | 39&40 | "$(CH_2)$-$n_1$-$CH_2Hal$" | --$(CH_2)_{n_1}$-$CH_2Hal$-- |
| 7 | Scheme 2 | 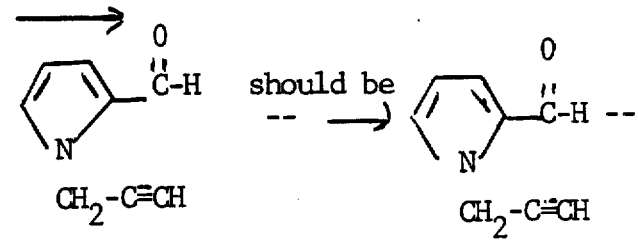 should be 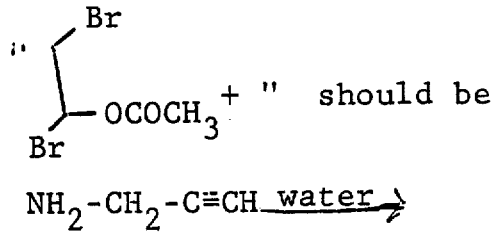 | |
| 8 | Scheme 4 | 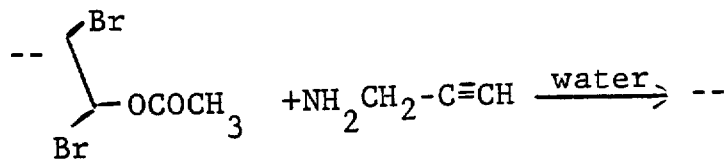 | |

UNITED STATES PATENT AND TRADEMARK OFFICE
CERTIFICATE OF CORRECTION

PATENT NO. : 4,737,513

DATED : April 12, 1988

INVENTOR(S) : JEAN TESSIER, JEAN-PIERRE DEMOUTE and LAURENT TALIANI

It is certified that error appears in the above-identified patent and that said Letters Patent is hereby corrected as shown below:

Col.　　Line

11　　Scheme 13　　　　"AR-O-CH(N(CH$_3$)$_2$"　　should be

-- +AR-O-CH(N(CH$_3$)$_2$ --

11　　　"　　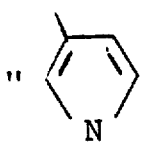　"　　should be --　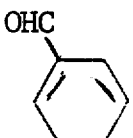　--

13　　Scheme 14　　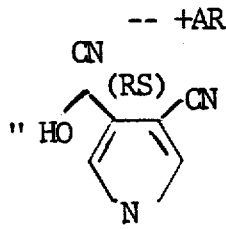　"　　should be　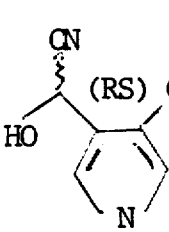

UNITED STATES PATENT AND TRADEMARK OFFICE
CERTIFICATE OF CORRECTION

PATENT NO. : 4,737,513  
DATED : April 12, 1988  
INVENTOR(S) : JEAN TESSIER, JEAN-PIERRE DEMOUTE and LAURENT TALIANI It is certified that error appears in the above-identified patent and that said Letters Patent is hereby corrected as shown below:

Col. Line  
22   60   " 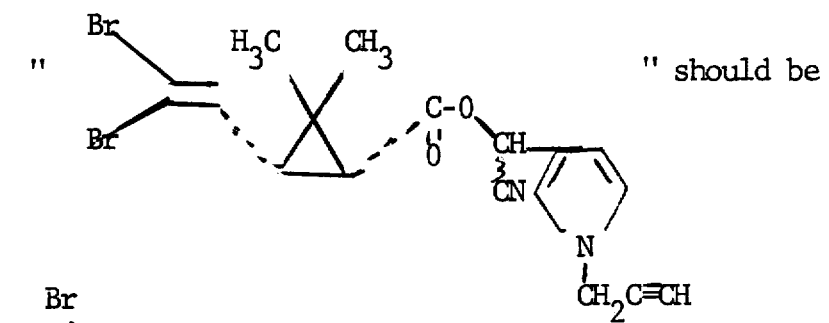 " should be

-- 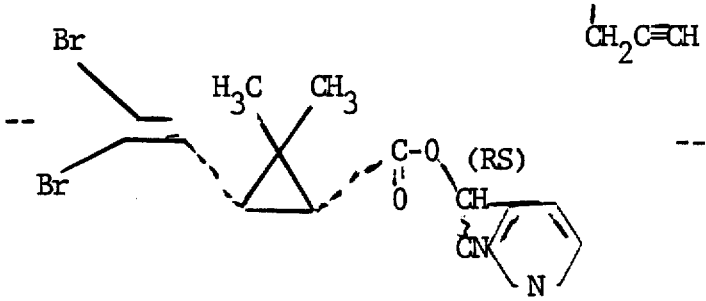 --

25   5   " 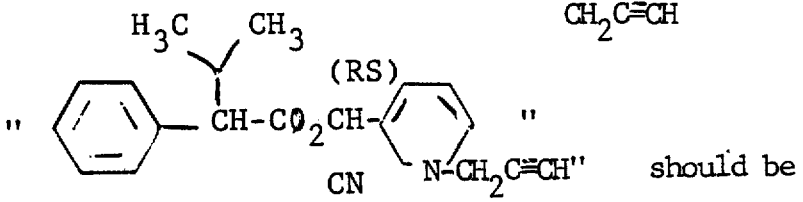 " should be

-- 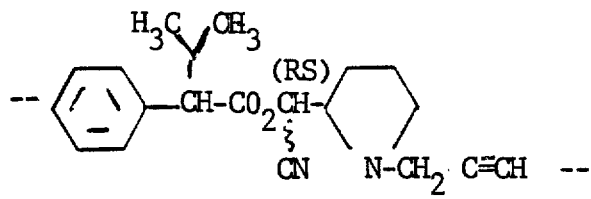 --

UNITED STATES PATENT AND TRADEMARK OFFICE
CERTIFICATE OF CORRECTION

PATENT NO. : 4,737,513

DATED : April 12, 1988

INVENTOR(S) : JEAN TESSIER, JEAN-PIERRE DEMOUTE and LAURENT TALIANI

It is certified that error appears in the above-identified patent and that said Letters Patent is hereby corrected as shown below:

| Col. | Line | | | |
|---|---|---|---|---|
| 29 | 68 | "cyclohexaneethyl" should be --cyclohexane-ethyl-- | | |
| 34 | 15 | " 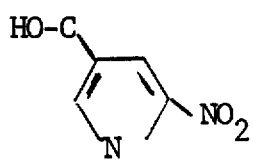 " should be -- 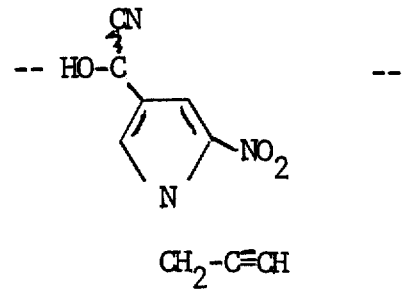 -- | | |
| 41 | 36&37 | "165°C" | should be | --165°C-- |
| 44 | 42&43 | "60°C" | " " | --60°C-- |
| 50 | 40 | "HO-C-<br>    |<br>    C<br>    ||<br>    C<br>    |<br>    H" | should be | --HO-C-<br>    |<br>    C<br>    |||<br>    C<br>    |<br>    H-- |

UNITED STATES PATENT AND TRADEMARK OFFICE
CERTIFICATE OF CORRECTION

PATENT NO. : 4,737,513
DATED : April 12, 1988
INVENTOR(S) : JEAN TESSIER, JEAN-PIERRE DEMOUTE and LAURENT TALLIANI It is certified that error appears in the above-identified patent and that said Letters Patent is hereby corrected as shown below:

| Col. | Line | | | |
|---|---|---|---|---|
| 50 | 50 | "HO-C- with H above, C below, C=C, H below" | should be | --HO-C- with circled H above, C below, C=C, circled H below-- |
| 58 | 30 | [structure with F, (E), OEt, 1R,cis, CN, NC, CH₂-C≡CH] | should be | [corrected structure] |
| 55 | 37 | "60° C" | should be | --60°C-- |
| 55 | 39 | "60°" C | should be | --60°C-- |
| 55 | 43 | "60° C" | should be | --60°C-- |

UNITED STATES PATENT AND TRADEMARK OFFICE
CERTIFICATE OF CORRECTION

PATENT NO. : 4,737,513

DATED : April 12, 1988

INVENTOR(S) : JEAN TESSIER, JEAN-PIERRE DEMOUTE and LAURENT TALLIANI

It is certified that error appears in the above-identified patent and that said Letters Patent is hereby corrected as shown below:

| Col. | Line | | |
|---|---|---|---|
| 57 | 52 | "20° C" | should be --20°C-- |
| 66 | Claim 2 | "$CH_2\text{-}C\equiv CH$" | should be -- $-CH_2\text{-}C\equiv CH$-- |
| 67 | Claim 8 | "$R_1$, $R_4$ and $R_5$" | should be --$R_2$, $R_4$ and $R_5$-- |
| 67 | Claim 18 | "$-CH_2\text{-}C\equiv CH$" | should be --$CH_2\text{-}C\equiv CH$ -- |
| 69 | Claim 35 | " " " " " " " " " " " " " " " " " " " | |

Signed and Sealed this

Twenty-first Day of March, 1989

Attest:

DONALD J. QUIGG

*Attesting Officer*  *Commissioner of Patents and Trademarks*